US008729231B2

(12) United States Patent
Bussfeld et al.

(10) Patent No.: US 8,729,231 B2
(45) Date of Patent: May 20, 2014

(54) SURFACE ANTIGEN PROTEIN MUTANT OF HEPATITIS B VIRUS SURFACE ANTIGEN

(75) Inventors: Delia Bussfeld, Marburg (DE); Anne-Sophie Endres, Berlin (DE); Helga Meisel, Berlin (DE); Michael Weik, Coelbe (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 812 days.

(21) Appl. No.: 12/809,983

(22) PCT Filed: Dec. 16, 2008

(86) PCT No.: PCT/EP2008/010708
§ 371 (c)(1),
(2), (4) Date: Oct. 12, 2010

(87) PCT Pub. No.: WO2009/083136
PCT Pub. Date: Jul. 9, 2009

(65) Prior Publication Data
US 2011/0033838 A1      Feb. 10, 2011

(30) Foreign Application Priority Data
Dec. 21, 2007    (DE) .................... 10 2007 062 962

(51) Int. Cl.
*A61K 39/00*      (2006.01)
*C07K 14/005*     (2006.01)

(52) U.S. Cl.
USPC ........ 530/350; 435/320.1; 435/69.3; 435/7.9; 536/23.72

(58) Field of Classification Search
None
See application file for complete search history.

(56) References Cited

U.S. PATENT DOCUMENTS

| | | | |
|---|---|---|---|
| 7,745,130 B2 * | 6/2010 | Bartholomeusz et al. | 435/5 |
| 2007/0042356 A1 | 2/2007 | Schildgen et al. | 435/5 |

FOREIGN PATENT DOCUMENTS

| | | | | |
|---|---|---|---|---|
| WO | 03/087351 A | 10/2003 | ............... | C12N 7/00 |
| WO | WO 03/087351 A1 * | 10/2003 | ............... | C12N 7/00 |
| WO | 2004/113370 A | 12/2004 | ............... | C07K 14/02 |
| WO | 2005/042733 A | 5/2005 | ............... | C12N 7/00 |

OTHER PUBLICATIONS

Meisel, H. et al., "Transmission of Hepatitis B Virus 2 Months Prior to Hepatitis Surface Antigen Positivity of Donor Blood", Transfusion Medicine and Hemotherapy, vol. 30, No. 5, pp. 228-231, XP08105773, 2003.
Marschenz et al., "Functional Analysis of Complex Hepatitis B Virus Variants Associated with Development of Liver Cirrhosis", Gastroenterology, vol. 131, No. 3, pp. 765-780, XP005659135, Sep. 1, 2006.
BLAST Basic Local Alignment Search Tool, Nucleotide Sequence, Graphic Summary—Distribution of 100 Blast Hits on the Query Sequence; 49 pages, 2012.
BLAST Basic Local Alignment Search Tool, Protein Sequence, Graphic Summary—Distribution of 100 Blast Hits on the Query Sequence; 6 pages, 2012.
DQ412279, QWB86_HB aus Hepatitis B Virus Isolate s02003094 S Protein gene, complete eds, http://ibis/IBIS/exam/dbfetch.jsp?id=EM_VI:DQ412279, 2 pages, Apr. 5, 2006.
Ghaemmaghami, S., et al., "Global Analysis of Protein Expression in Yeast", Letters to Nature, Nature, vol. 425; pp. 737-741, Oct. 16, 2003.
Hong, H., et al., "Antibody Engineering", Biotechnol, Bioprocess Eng., vol. 7, p. 150-154, 2002.
Lazarevic, I. et al., S Protein [Hepatitis B Virus], GenBank: ABM54618.1; 2 pages, 2006.
Lazarevic, I., et al., "Distribution of HBV Genotypes, Subgenotypes and HBsAg Subtypes Among Chronically Infected Patients in Serbia", Archives of Virology, vol. 152 No. 11, p. 2017-2025, Aug. 6, 2007.
Niesters, et al., GenBank:DQ412279.1, Hepatitis B Virus Isolate s02003094 S Protein gene, complete cds, 2006.
Report of Examination, European Patent Office, Eurropean Patent Application No. 08 869 063.1—1223; 7 pages, Jul. 1, 2011.
Wolters, G., et al., "Solid-Phase Enzyme-Immunoassay for Detection of Hepatitis B Surface Antigen", Organon Scientific Development Group, Oss, The Netherlands; J. Clin. Path., vol. 29; pp. 873-879, 1976.

* cited by examiner

*Primary Examiner* — Agnieszka Boesen
(74) *Attorney, Agent, or Firm* — King & Spalding L.L.P.

(57) ABSTRACT

The disclosure relates, in some embodiments, to sequences of a novel mutant or variant of the hepatitis B surface antigen (HBsAg) and methods for detecting this genome and protein variant, and antibodies directed against it, from patients' samples.

7 Claims, 6 Drawing Sheets

Fig. 1: Amino acid sequence of the HBsAg a determinant of the various HBV genotypes compared with the novel mutant HDB 07

A representative genome was used as basis for each genotype, and the aa sequence was derived from the nucleotide sequence
A: X02763; Ba: D00330; Bj: AB073858; C: AB033556; $C_{aus}$: AB048704; D: X02496; E: X75657; F: X69798; G: AF160501; H: AY090454
(Bartholomeusz and Schaefer; Rev. Med. Virol. 14: 3-16 (2004))

```
#aa        100        110        120        130        140        150        160        170        180
           |          |          |          |          |          |          |          |          |
Genotype
A          YQGMLPVCPL IPGSTTTSTG PCKTCTTPAQ GNSMFPSCCC TKPTDGNCTC IPIPSSWAFA KYLWEWASVR FSWLSLLVPF V
Ba         ---------- ----S----- ---------- -T-------- ---------- ---------- ---------- ---------- -
Bj         ---------- ----S----- ---------- -T-L------ ---------- ---------- ---------- ---------- -
C          ---------- L--TS----- ------I--- -T-------- ---S------ ---------- -F-------- ---------- -
Caus       ---------- L--------- --R---IT-- -T-------- ---S------ --------G- -F-------- ---------- -
D          ---------- ----S----- --R------- -T--Y----- ---S------ ---------G -F------A- ---------- -
E          ---------- ----S----- --R----L-- -T-------- S--S------ ---------G -F------A- ---------- -
F          ---------- L--------- -------L-- -T-------- S--S------ --------LG --------A- --------Q- -
G          ---------- ----S----- ---------- ----Y----- ---S------ ---------- ---------- ---------- -
H          ---------- L--------- -------L-- -T-------- ---S------ ---------G --------A- --------Q- -

HDB07      C----R---- L---S---R- L--------- -T--Y----- --LS------ ---------G NF------A- ---P------ -

#aa        100               118                       142                 160          173
                105    110         120
```

The seven amino acid replacements occurring in none of the representative sequences used as basis are emboldened

Fig. 2: Nucleotide sequence of the S gene X02496 (genotype D, subtype ayw2)

Consecutive numbering of nucleotides (nt) encoding the surface antigen (excluding pre S1 and pre S2 regions)

Consecutive numbering of amino acids (aa)

| | | | (aa) | (nt) |
|---|---|---|---|---|
| 1 | | ATG GAG AAC ATC ACA TCA GGA TTC CTA GGA CCC CTG CTC GTG TTA CAG GCG GGG TTT TTC | | 60 |
| | 1 | Met Glu Asn Ile Thr Ser Gly Phe Leu Gly Pro Leu Leu Val Leu Gln Ala Gly Phe Phe | 20 | |
| | | M E N I T S G F L G P L L V L Q A G F F | | |
| 61 | | TTG TTG ACA AGA ATC CTC ACA ATA CCG CAG AGT CTA GAC TCG TGG TGG ACT TCT CTC AAT | | 120 |
| | 21 | Leu Leu Thr Arg Ile Leu Thr Ile Pro Gln Ser Leu Asp Ser Trp Trp Thr Ser Leu Asn | 40 | |
| | | L L T R I L T I P Q S L D S W W T S L N | | |
| 121 | | TTT CTA GGG GGA ACT ACC GTG TGT CTT GGC CAA AAT TCG CAG TCC CCA ACC TCC AAT CAC | | 180 |
| | 41 | Phe Leu Gly Gly Thr Thr Val Cys Leu Gly Gln Asn Ser Gln Ser Pro Thr Ser Asn His | 60 | |
| | | F L G G T T V C L G Q N S Q S P T S N H | | |
| 181 | | TCA CCA ACC TCC TGT CCT CCA ACT TGT CCT GGT TAT CGC TGG ATG TGT CTG CGG CGT TTT | | 240 |
| | 61 | Ser Pro Thr Ser Cys Pro Pro Thr Cys Pro Gly Tyr Arg Trp Met Cys Leu Arg Arg Phe | 80 | |
| | | S P T S C P P T C P G Y R W M C L R R F | | |
| 241 | | ATC ATC TTC CTC TTC ATC CTG CTG CTA TGC CTC ATC TTC TTG TTG GTT CTT CTG GAC TAT | | 300 |
| | 81 | Ile Ile Phe Leu Phe Ile Leu Leu Leu Cys Leu Ile Phe Leu Leu Val Leu Leu Asp Tyr | 100 | |
| | | I I F L F I L L L C L I F L L V L L D Y | | |
| 301 | | CAA GGT ATG TTG CCC GTT TGT CCT CTA ATT CCA GGA TCT TCA ACT ACC AGC ACG GGA CCA | | 360 |
| | 101 | Gln Gly Met Leu Pro Val Cys Pro Leu Ile Pro Gly Ser Ser Thr Thr Ser Thr Gly Pro | 120 | |
| | | Q G M L P V C P L I P G S S T T S T G P | | |
| 361 | | TGC AGA ACC TGC ACG ACT CCT GCT CAA GGA ACC TCT ATG TAT CCC TCC TGT TGC TGT ACC | | 420 |
| | 121 | Cys Arg Thr Cys Thr Thr Pro Ala Gln Gly Thr Ser Met Tyr Pro Ser Cys Cys Cys Thr | 140 | |
| | | C R T C T T P A Q G T S M Y P S C C C T | | |
| 421 | | AAA CCT TCG GAC GGA AAT TGC ACC TGT ATT CCC ATC CCA TCA TCC TGG GCT TTC GGA AAA | | 480 |
| | 141 | Lys Pro Ser Asp Gly Asn Cys Thr Cys Ile Pro Ile Pro Ser Ser Trp Ala Phe Gly Lys | 160 | |
| | | K P S D G N C T C I P I P S S W A F G K | | |
| 481 | | TTC CTA TGG GAG TGG GCC TCA GCC CGT TTC TCC TGG CTC AGT TTA CTA GTG CCA TTT GTT | | 540 |
| | 161 | Phe Leu Trp Glu Trp Ala Ser Ala Arg Phe Ser Trp Leu Ser Leu Leu Val Pro Phe Val | 180 | |
| | | F L W E W A S A R F S W L S L L V P F V | | |
| 541 | | CAG TGG TTC GTA GGG CTT TCC CCC ACT GTT TGG CTT TCA GTT ATA TGG ATG ATG TGG TAT | | 600 |
| | 181 | Gln Trp Phe Val Gly Leu Ser Pro Thr Val Trp Leu Ser Val Ile Trp Met Met Trp Tyr | 200 | |
| | | Q W F V G L S P T V W L S V I W M M W Y | | |
| 601 | | TGG GGG CCA AGT CTG TAC AGC ATC TTG AGT CCC TTT TTA CCG CTG TTA CCA ATT TTC TTC | | 660 |
| | 201 | Trp Gly Pro Ser Leu Tyr Ser Ile Leu Ser Pro Phe Leu Pro Leu Leu Pro Ile Phe Phe | 220 | |
| | | W G P S L Y S I L S P F L P L L P I F F | | |
| 661 | | TGT CTT TGG GTA TAC ATT | | 678 |
| | 221 | Cys Leu Trp Val Tyr Ile | 226 | |
| | | C L W V Y I | | |

Fig. 3: Nucleotide sequence of the HBV surface antigen-encoding S gene of the wild type HBV, genotype D/ayw2 [X02496] (upper sequence from nt 1 to nt 678) compared with the nucleotide sequence of the novel variant HDB 07 (lower sequence, in which nucleotide differences are emboldened and parenthesized if the mutations do not lead to an amino acid exchange)

| | | |
|---|---|---|
| 1 | ATG GAG AAC ATC ACA TCA GGA TTC CTA GGA CCC CTG CTC GTG TTA CAG GCG GGG TTT TTC | 60 |
| | ATG GAG AAC ATC ACA TCA GGA TTC CTA GGA CCC CTG CTC GTG TTA CAG GCG GGG TTT TTC | |
| 61 | TTG TTG ACA AGA ATC CTC ACA ATA CCG CAG AGT CTA GAC TCG TGG TGG ACT TCT CTC AAT | 120 |
| | TTG TTG ACA AGA ATC CTC ACA ATA CCG CAG AGT CTA GAC TCG TGG TGG ACT TCT CTC AAT | |
| 121 | TTT CTA GGG GGA ACT ACC GTG TGT CTT GGC CAA AAT TCG CAG TCC CCA ACC TCC AAT CAC | 180 |
| | TTT CTA GGG GGA ACT ACC GTG TGT CTT GGC CAA AAT TCG CAG TCC CCA ACC TCC AAT CAC | |
| 181 | TCA CCA ACC TCC TGT CCT CCA ACT TGT CCT GGT TAT CGC TGG ATG TGT CTG CGG CGT TTT | 240 |
| | TCA CCA ACC TCC TGT CCT CCA ACT TGT CCT GGT TAT CGC TGG ATG TGT CTG CGG CGT TTT | |
| 241 | ATC ATC TTC CTC TTC ATC CTG CTG CTA TGC CTC ATC TTC TTG TTG GTT CTT CTG GAC TAT | 300 |
| | ATC ATC TTC CTC TTC ATC CTG CTG CTA TGC CTC ATC TTC TTG TTG GTT CTT CTG GAC **TGT** | |
| 301 | CAA GGT ATG TTG CCC GTT TGT CCT CTA ATT CCA GGA TCT TCA ACT ACC AGC ACG GGA CCA | 360 |
| | CAA GGT ATG (**TTA**) **CGC** GTT TGT CCT CTA **CTT** CCA GGA TCT TCA (**ACC**) ACC AGC **AGG** GGA **CTA** | |
| 361 | TGC AGA ACC TGC ACG ACT CCT GCT CAA GGA ACC TCT ATG TAT CCC TCC TGT TGC TGT ACC | 420 |
| | TGC **AAA** ACC TGC ACG ACT CCT GCT CAA GGA ACC TCT ATG TAT CCC TCC TGT TGC TGT ACC | |
| 421 | AAA CCT TCG GAC GGA AAT TGC ACC TGT ATT CCC ATC CCA TCA TCC TGG GCT TTC GGA AAA | 480 |
| | AAA **CTT** TCG GAC GGA AAT TGC ACC TGT ATT CCC ATC CCA TCA TCC TGG GCT TTC GGA **AAC** | |
| 481 | TTC CTA TGG GAG TGG GCC TCA GCC CGT TTC TCC TGG CTC AGT TTA CTA GTG CCA TTT GTT | 540 |
| | TTC CTA TGG GAG TGG GCC TCA GCC CGT TTC TCC TGG **CCC** AGT TTA CTA GTG CCA TTT GTT | |
| 541 | CAG TGG TTC GTA GGG CTT TCC CCC ACT GTT TGG CTT TCA GTT ATA TGG ATG ATG TGG TAT | 600 |
| | CAG TGG TTC GTA GGG CTT TCC CCC ACT GTT TGG CTT TCA GTT ATA TGG ATG ATG TGG TAT | |
| 601 | TGG GGG CCA AGT CTG TAC AGC ATC TTG AGT CCC TTT TTA CCG CTG TTA CCA ATT TTC TTC | 660 |
| | TGG GGG CCA AGT CTG TAC AGC ATC TTG AGT CCC TTT TTA CCG CTG TTA CCA ATT TTC **TTT** | |
| 661 | TGT CTT TGG GTA TAC ATT 678 | |
| | TGT CTT TGG GTA TAC ATT | |

Fig. 4: Nucleotide sequence (nt 1 to nt 678) of the S gene of the novel HBV variant HDB 07.
Only the nucleotide differences which lead to an alteration in the amino acid sequence are emboldened (compared with the genotype D/ayw2; X02496).

| | | |
|---|---|---|
| 1 | ATG GAG AAC ATC ACA TCA GGA TTC CTA GGA CCC CTG CTC GTG TTA CAG GCG GGG TTT TTC | 60 |
| 61 | TTG TTG ACA AGA ATC CTC ACA ATA CCG CAG AGT CTA GAC TCG TGG TGG ACT TCT CTC AAT | 120 |
| 121 | TTT CTA GGG GGA ACT ACC GTG TGT CTT GGC CAA AAT TCG CAG TCC CCA ACC TCC AAT CAC | 180 |
| 181 | TCA CCA ACC TCC TGT CCT CCA ACT TGT CCT GGT TAT CGC TGG ATG TGT CTG CGG CGT TTT | 240 |
| 241 | ATC ATC TTC CTC TTC ATC CTG CTG CTA TGC CTC ATC TTC TTG TTG GTT CTT CTG GAC **TGT** | 300 |
| 301 | CAA GGT ATG TTA **CGC** GTT TGT CCT CTA **CTT** CCA GGA TCT TCA ACC ACC AGC **AGG** GGA **CTA** | 360 |
| 361 | TGC **AAA** ACC TGC ACG ACT CCT GCT CAA GGA ACC TCT ATG TAT CCC TCC TGT TGC TGT ACC | 420 |
| 421 | AAA **CTT** TCG GAC GGA AAT TGC ACC TGT ATT CCC ATC CCA TCA TCC TGG GCT TTC GGA **AAC** | 480 |
| 481 | TTC CTA TGG GAG TGG GCC TCA GCC CGT TTC TCC TGG **CCC** AGT TTA CTA GTG CCA TTT GTT | 540 |
| 541 | CAG TGG TTC GTA GGG CTT TCC CCC ACT GTT TGG CTT TCA GTT ATA TGG ATG ATG TGG TAT | 600 |
| 601 | TGG GGG CCA AGT CTG TAC AGC ATC TTG AGT CCC TTT TTA CCG CTG TTA CCA ATT TTC TTT | 660 |
| 661 | TGT CTT TGG GTA TAC ATT | 678 |

Fig. 5: S gene nucleotide sequence (1 to 678) and corresponding amino acid sequence (aa 1 to 226) of the novel HBV variant HDB 07 (amino acids which are replaced compared with the wild type HBV, genotype D/ayw2 [X02496], are emboldened and underlined)

```
1       ATG GAG AAC ATC ACA TCA GGA TTC CTA GGA CCC CTG CTC GTG TTA CAG GCG GGG TTT TTC     60
    1    M   E   N   I   T   S   G   F   L   G   P   L   L   V   L   Q   A   G   F   F   20

61      TTG TTG ACA AGA ATC CTC ACA ATA CCG CAG AGT CTA GAC TCG TGG TGG ACT TCT CTC AAT    120
   21    L   L   T   R   I   L   T   I   P   Q   S   L   D   S   W   W   T   S   L   N   40

121     TTT CTA GGG GGA ACT ACC GTG TGT CTT GGC CAA AAT TCG CAG TCC CCA ACC TCC AAT CAC    180
   41    F   L   G   G   T   T   V   C   L   G   Q   N   S   Q   S   P   T   S   N   H   60

181     TCA CCA ACC TCC TGT CCT CCA ACT TGT CCT GGT TAT CGC TGG ATG TGT CTG CGG CGT TTT    240
   61    S   P   T   S   C   P   P   T   C   P   G   Y   R   W   M   C   L   R   R   F   80

241     ATC ATC TTC CTC TTC ATC CTG CTG CTA TGC CTC ATC TTC TTG TTG GTT CTT CTG GAC TGT    300
   81    I   I   F   L   F   I   L   L   L   C   L   I   F   L   L   V   L   L   D   C  100

301     CAA GGT ATG TTA CGC GTT TGT CCT CTA CTT CCA GGA TCT TCA ACC ACC AGC AGG GGA CTA    360
  101    Q   G   M   L   R   V   C   P   L   L   P   G   S   S   T   T   S   R   G   L  120

361     TGC AAA ACC TGC ACG ACT CCT GCT CAA GGA ACC TCT ATG TAT CCC TCC TGT TGC TGT ACC    420
  121    C   K   T   C   T   T   P   A   Q   G   T   S   M   Y   P   S   C   C   C   T  140

421     AAA CTT TCG GAC GGA AAT TGC ACC TGT ATT CCC ATC CCA TCA TCC TGG GCT TTC GGA AAC    480
  141    K   L   S   D   G   N   C   T   C   I   P   I   P   S   S   W   A   F   G   N  160

481     TTC CTA TGG GAG TGG GCC TCA GCC CGT TTC TCC TGG CCC AGT TTA CTA GTG CCA TTT GTT    540
  161    F   L   W   E   W   A   S   A   R   F   S   W   P   S   L   L   V   P   F   V  180

541     CAG TGG TTC GTA GGG CTT TCC CCC ACT GTT TGG CTT TCA GTT ATA TGG ATG ATG TGG TAT    600
  181    Q   W   F   V   G   L   S   P   T   V   W   L   S   V   I   W   M   M   W   Y  200

601     TGG GGG CCA AGT CTG TAC AGC ATC TTG AGT CCC TTT TTA CCG CTG TTA CCA ATT TTC TTT    660
  201    W   G   P   S   L   Y   S   I   L   S   P   F   L   P   L   L   P   I   F   F  220

661     TGT CTT TGG GTA TAC ATT    678
  221    C   L   W   V   Y   I    226
```

The following aa are replacements (X) in the HDB 07 variant compared with the wild type HBV (genotype D/ayw2):

Y 100 (C), P 105 (R), I 110 (L), T 118 (R), P 120 (L), R 122 (K) (change of the subtype-determining determinant from ad to ay), P 142 (L), K 160 (N), (loss of the additional determinant w), and L 173 (P).

Fig. 6: Comparison of the amino acid sequences of the a determinant (aa 100 to aa 180) of the novel variant HDB 07 (lower sequence) with the wild type HBV, genotype D/ayw2 [X02496] (upper sequence)

aa sequence of wild type D/ayw2 [X02496]: Y 100
aa sequence of variant HDB 07: C

| | | | | | | | | | | | | | | | | | | | | | |
|---|---|---|---|---|---|---|---|---|---|---|---|---|---|---|---|---|---|---|---|---|---|
| 101 | Q | G | M | L | P | V | C | P | L | I | P | G | S | S | T | T | S | T | G | P | 120 |
| | Q | G | M | L | R | V | C | P | L | L | P | G | S | S | T | T | S | R | G | L | |
| 121 | C | R | T | C | T | T | P | A | Q | G | T | S | M | Y | P | S | C | C | C | T | 140 |
| | C | K | T | C | T | T | P | A | Q | G | T | S | M | Y | P | S | C | C | C | T | |
| 141 | K | P | S | D | G | N | C | T | C | I | P | I | P | S | S | W | A | F | G | K | 160 |
| | K | L | S | D | G | N | C | T | C | I | P | I | P | S | S | W | A | F | G | N | |
| 161 | F | L | W | E | W | A | S | A | R | F | S | W | L | S | L | L | V | P | F | V | 180 |
| | F | L | W | E | W | A | S | A | R | F | S | W | P | S | L | L | V | P | F | V | |
| 181 | Q | W | F | V | G | L | S | P | T | V | 190 | | | | | | | | | | |
| | Q | W | F | V | G | L | S | P | T | V | | | | | | | | | | | |

The following aa are replacements (X) in the HDB 07 variant compared with the wild type HBV (genotype D/ayw2):
Y 100 (C), P 105 (R), I (110) L, T 118 (R), P 120 (L), R 122 (K) (change of the subtype-determining determinant from ad to ay), P 142 (L), K 160 (N), (loss of the additional determinant w), and L 173 (P).

SURFACE ANTIGEN PROTEIN MUTANT OF HEPATITIS B VIRUS SURFACE ANTIGEN

CROSS-REFERENCE TO RELATED APPLICATIONS

This application claims priority to PCT Application No. PCT/EP2008/010708 filed Dec. 16, 2008, now published as WO 2009/083136, which claims priority to German Patent Application No. 10 2007 062 962.3, filed Dec. 21, 2007. The contents of all of the above are hereby incorporated in their entirety by reference.

FIELD OF THE DISCLOSURE

The present disclosure relates, in some embodiments, to compositions, systems, and methods for diagnosis, vaccination, and/or treatment of HBV.

BACKGROUND OF THE DISCLOSURE

Hepatitis B virus (HBV) is well known to induce disorders with a multiplicity of courses, from infections with mild, inapparent courses to chronically active inflammations of the liver (viral hepatitis) having fulminant courses. Chronic infection with HBV represents a global health problem, with 400 million people estimated to be affected (Lee, N. Engl. J. Med. 337; 1733-1745 (1997)). The most suitable prophylactic measures for HBV infection, which is to be encountered frequently around the world, are regarded as being active immunization (stimulation of the antibody response through administration of antigen) and also passive immunization (by injection of preformed antibodies).

SUMMARY

Accordingly, a need has arisen for improved compositions, systems, and methods for diagnosis, vaccination, and/or treatment of HBV. The present disclosure relates, according to some embodiments, to an oligopeptide and/or polypeptide comprising an amino acid sequence selected from the group consisting of: (a) an amino acid sequence which has at least 92% identity with SEQ ID No: 5; (b) an amino acid sequence in which zero to six amino acids in SEQ ID No: 5 are replaced, deleted or inserted; and (c) an amino acid sequence which is a partial sequence of SEQ ID No: 3 having at least 5 consecutive amino acids of SEQ ID No: 3 (e.g., at least 6 or at least 7 or at least 8 or at least 9 or at least 10 or at least 11 or at least 12 or at least 13 or at least 14 or at least 15 consecutive amino acids of SEQ ID No: 3), where this partial sequence includes at least one of positions 100, 105, 110, 118, 120, 142, 160 and 173 of SEQ ID No: 3. For example, an oligopeptide and/or polypeptide may comprise an amino acid sequence which is selected from the group consisting of SEQ ID No: 3, SEQ ID No: 4 and SEQ ID No: 5. In some embodiments, an oligopeptide and/or polypeptide may react with sera from individuals infected by the hepatitis B variant HDB 07. An oligopeptide and/or polypeptide may be included in a composition in some embodiments. For example, a composition may comprise an immunogenic peptide and/or mixture of immunogenic peptides comprising one or more of the oligopeptides and/or polypeptides. An oligopeptide and/or polypeptide may comprise a fragment of an HBs antigen of a hepatitis B virus according to some embodiments. For example, an oligopeptide and/or polypeptide may comprise a fragment of an HBs antigen of a hepatitis B virus, wherein (i) a length of at least 5 amino acids (e.g., at least 6 or at least 7 or at least 8 or at least 9 or at least 10 or at least 11 or at least 12 or at least 13 or at least 14 or at least 15 amino acids), (ii) the HBs antigen has cysteine at position 100, arginine at position 105, leucine at position 110, arginine at position 118, leucine at position 120, leucine at position 142, asparagine at position 160 and proline at position 173, and/or (iii) the fragment comprises cysteine 100, arginine 105, leucine 110, arginine 118, leucine 120, leucine 142, asparagine 160 and/or proline 173.

The present disclosure also relates, in some embodiments, to an oligonucleotide and/or polynucleotide comprising a nucleic acid sequence selected from the group consisting of (a) a nucleotide sequence which has at least 95.8% identity with SEQ ID No: 2, (b) a nucleotide sequence in which zero to nucleotides are replaced, deleted or added by comparison with SEQ ID No: 2, (c) a nucleotide sequence which is a partial sequence of SEQ ID No: 1 having at least 8 consecutive nucleotides of SEQ ID No: 1 (e.g., at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or at least 30 consecutive nucleotides of SEQ ID No: 1), where the partial sequence includes at least one of positions 298, 299, 300, 310, 311, 312, 313, 314, 315, 328, 329, 330, 343, 344, 345, 352, 353, 354, 358, 359, 360, 364, 365, 366, 424, 425, 426, 517, 518 and 519 of SEQ ID No: 1; (d) a nucleotide sequence which hybridizes under stringent conditions specifically with a polynucleotide complementary to the sequence SEQ ID No: 1; (e) a nucleotide sequence which codes for an oligo- or polypeptide as claimed in any of claims 1 to 3; and compliments thereof. For example, an oligonucleotide and/or polynucleotide may comprise a nucleic acid sequence consisting of SEQ ID No: 2. According to some embodiments, an oligonucleotide and/or polynucleotide may have a length of from 10 to 30 nucleotides. The present disclosure further relates to vectors, plasmids, and/or cells comprising an oligonucleotide and/or polynucleotide as described herein.

The present disclosure further relates, in some embodiments, to a method for preparing an oligopeptide and/or polypeptide comprising culturing a cell under suitable conditions such that the oligopeptide and/or polypeptide is produced (e.g., expressed). For example, the cell may comprise an oligonucleotide and/or polynucleotide (e.g., in a vector or plasmid) encoding an oligopeptide and/or polypeptide comprising an amino acid sequence selected from the group consisting of: (a) an amino acid sequence which has at least 92% identity with SEQ ID No: 5; (b) an amino acid sequence in which zero to six amino acids in SEQ ID No: 5 are replaced, deleted or inserted; and (c) an amino acid sequence which is a partial sequence of SEQ ID No: 3 having at least 5 consecutive amino acids of SEQ ID No: 3 (e.g., at least 6 or at least 7 or at least 8 or at least 9 or at least 10 or at least 11 or at least 12 or at least 13 or at least 14 or at least 15 consecutive amino acids of SEQ ID No: 3), where this partial sequence includes at least one of positions 100, 105, 110, 118, 120, 142, 160 and 173 of SEQ ID No: 3. According to some embodiments, a method may include obtaining the oligopeptide and/or polypeptide from the cell and/or separating it from other oligopeptides and/or polypeptides.

The present disclosure also relates to an antibody that binds to an oligopeptide and/or polypeptide comprising an amino acid sequence selected from the group consisting of: (a) an amino acid sequence which has at least 92% identity with SEQ ID No: 5; (b) an amino acid sequence in which zero to six amino acids in SEQ ID No: 5 are replaced, deleted or inserted; and (c) an amino acid sequence which is a partial sequence of SEQ ID No: 3 having at least 5 consecutive amino acids of SEQ ID No: 3 (e.g., at least 6 or at least 7 or at least 8 or at least 9 or at least 10 or at least 11 or at least 12 or at least 13 or at least 14 or at least 15 consecutive amino acids of SEQ ID No: 3), where this partial sequence includes at least one of positions 100, 105, 110, 118, 120, 142, 160 and 173 of SEQ ID No: 3. An antibody may bind to the oligopeptide and/or polypeptide more strongly than it binds to HBs antigen of a hepatitis B virus of genotype D, subtype ayw2, according to some embodiments.

The present disclosure further relates, in some embodiments, to an anti-idiotype antibody which represents an oligopeptide and/or polypeptide comprising an amino acid sequence selected from the group consisting of: (a) an amino acid sequence which has at least 92% identity with SEQ ID No: 5; (b) an amino acid sequence in which zero to six amino acids in SEQ ID No: 5 are replaced, deleted or inserted; and (c) an amino acid sequence which is a partial sequence of SEQ ID No: 3 having at least 5 consecutive amino acids of SEQ ID No: 3 (e.g., at least 6 or at least 7 or at least 8 or at least 9 or at least 10 or at least 11 or at least 12 or at least 13 or at least 14 or at least 15 consecutive amino acids of SEQ ID No: 3), where this partial sequence includes at least one of positions 100, 105, 110, 118, 120, 142, 160 and 173 of SEQ ID No: 3.

The present disclosure further relates, in some embodiments, to an assay kit for detecting hepatitis B viruses, comprising:

- (i) an oligopeptide and/or polypeptide comprising an amino acid sequence selected from the group consisting of:
  - (a) an amino acid sequence which has at least 92% identity with SEQ ID No: 5;
  - (b) an amino acid sequence in which zero to six amino acids in SEQ ID No: 5 are replaced, deleted or inserted; and
  - (c) an amino acid sequence which is a partial sequence of SEQ ID No: 3 having at least 5 consecutive amino acids of SEQ ID No: 3 (e.g., at least 6 or at least 7 or at least 8 or at least 9 or at least 10 or at least 11 or at least 12 or at least 13 or at least 14 or at least 15 consecutive amino acids of SEQ ID No: 3), where this partial sequence includes at least one of positions 100, 105, 110, 118, 120, 142, 160 and 173 of SEQ ID No: 3;
- (ii) an oligonucleotide and/or polynucleotide a nucleotide sequence selected from the group consisting of:
  - (a) a nucleotide sequence which has at least 95.8% identity with SEQ ID No: 2,
  - (b) a nucleotide sequence in which zero to 10 nucleotides are replaced, deleted or added by comparison with SEQ ID No: 2,
  - (c) a nucleotide sequence which is a partial sequence of SEQ ID No: 1 having at least 8 consecutive nucleotides of SEQ ID No: 1 (e.g., at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or at least 30 consecutive nucleotides of SEQ ID No: 1), where the partial sequence includes at least one of positions 298, 299, 300, 310, 311, 312, 313, 314, 315, 328, 329, 330, 343, 344, 345, 352, 353, 354, 358, 359, 360, 364, 365, 366, 424, 425, 426, 517, 518 and 519 of SEQ ID No: 1;
  - (d) a nucleotide sequence which hybridizes under stringent conditions specifically with a polynucleotide complementary to the sequence SEQ ID No: 1, or;
  - (e) a nucleotide sequence which codes for an oligo- or polypeptide as claimed in any of claims 1 to 3; and compliments thereof;
- (iii) an antibody which binds to an oligopeptide and/or polypeptide comprising an amino acid sequence selected from the group consisting of:
  - (a) an amino acid sequence which has at least 92% identity with SEQ ID No: 5;
  - (b) an amino acid sequence in which zero to six amino acids in SEQ ID No: 5 are replaced, deleted or inserted; and
  - (c) an amino acid sequence which is a partial sequence of SEQ ID No: 3 having at least 5 or at least 6 or at least 7 or at least 8 or at least 9 or at least 10 or at least 11 or at least 12 or at least 13 or at least 14 or at least 15 consecutive amino acids of SEQ ID No: 3, where this partial sequence includes at least one of positions 100, 105, 110, 118, 120, 142, 160 and 173 of SEQ ID No: 3; and/or
- (iv) an anti-idiotype antibody which represents an oligopeptide and/or polypeptide comprising an amino acid sequence selected from the group consisting of:
  - (a) an amino acid sequence which has at least 92% identity with SEQ ID No: 5;
  - (b) an amino acid sequence in which zero to six amino acids in SEQ ID No: 5 are replaced, deleted or inserted; and
  - (c) an amino acid sequence which is a partial sequence of SEQ ID No: 3 having at least 5 consecutive amino acids of SEQ ID No: 3 (e.g., at least 6 or at least 7 or at least 8 or at least 9 or at least 10 or at least 11 or at least 12 or at least 13 or at least 14 or at least 15 consecutive amino acids of SEQ ID No: 3), where this partial sequence includes at least one of positions 100, 105, 110, 118, 120, 142, 160 and 173 of SEQ ID No: 3.

The present disclosure also relates, in some embodiments, to a method for detecting a hepatitis B virus antigen comprising incubating a sample with an antibody as disclosed herein under conditions which allow the formation of an antigen-antibody complex comprising the antibody and detecting the antigen-antibody complex. The present disclosure further relates to a method for detecting antibodies directed against a hepatitis B virus antigen comprising incubating a sample with an oligopeptide and/or polypeptide as disclosed herein under conditions which allow the formation of an antigen-antibody complex comprising the oligopeptide and/or polypeptide and detecting the antibody-antigen complex, according to some embodiments.

The present disclosure also relates, in some embodiments, to a method for detecting a hepatitis B virus nucleic acid comprising incubating a sample with an oligonucleotide and/or polynucleotide as disclosed herein under conditions which allow selective hybridization of the oligonucleotide and/or polynucleotide with a hepatitis B virus nucleic acid in the sample and determining whether polynucleotide duplexes which include the oligonucleotide and/or polynucleotide have been formed. The present disclosure further relates, in some embodiments, to a method for detecting a hepatitis B virus nucleic acid comprising incubating a sample with an oligonucleotide and/or polynucleotide as disclosed herein under conditions which allow selective hybridization of the oligonucleotide and/or polynucleotide with a hepatitis B virus nucleic acid in the sample, carrying out a polymerase chain reaction, and determining whether a nucleic acid has been amplified.

The present disclosure further relates, in some embodiments, to an isolated hepatitis B virus that includes an HBs antigen. For example, an isolated hepatitis B virus may include an HBs antigen that comprises an amino acid sequence having at least 92% identity with SEQ ID No: 5.

BRIEF DESCRIPTION OF THE DRAWINGS

Some embodiments of the disclosure may be understood by referring, in part, to the present disclosure and the accompanying drawings, wherein:

FIG. 1 illustrates an overview of the amino acid sequences of the a determinant of 8 described genotypes of HBV compared with the HDB 07 variant according to a specific example embodiment of the disclosure.

FIG. 2 illustrates the nucleotide and amino acid sequences of the S gene of genotype D, subtype ayw2 of HBV according to a specific example embodiment of the disclosure.

FIG. 3 illustrates the nucleotide sequence of the HBV surface antigen for subtype ayw2 of genotype D of HBV, compared with the nucleotide sequence of HDB 07 according to a specific example embodiment of the disclosure.

FIG. 4 illustrates the translation-relevant differences in the nucleotide sequence of HDB 07 according to a specific example embodiment of the disclosure.

FIG. 5 illustrates the nucleotide sequence of the S gene of HDB 07 and the corresponding amino acid sequence according to a specific example embodiment of the disclosure. The a determinant is located between amino acid No. 101 and 180 of the small HBsAg (Small, S).

FIG. 6 illustrates the corresponding polypeptide sequence of the a determinant of HDB 07, and closely adjacent regions which are encoded by the nucleotide sequence described in FIG. 5 according to a specific example embodiment of the disclosure. These are compared with analogous regions of the subtype ayw2 of genotype D of HBV.

The disclosure relates, in some embodiments to sequences of a novel mutant or variant of the hepatitis B surface antigen (HBsAg) and methods for detecting this genome and protein variant, and antibodies directed against it, from patients' samples.

The novel sequences lead to 7 amino acid exchanges (replacements) in this combination not previously known in the hepatitis B surface antigen, HBsAg, in the region of amino acid positions 100 to 180 of the amino acid sequence of the surface antigen, with six substitutions being located in the region of the a determinant (aa 101 to aa 180) and one substitution in the direct neighborhood thereof (aa 100).

The disclosure also relates, in some embodiments to immunochemical detection methods for simultaneous detection of this novel HBV variant together with known variants/subtypes, and to the use of the novel sequences in conjunction with known sequences for simultaneous detection of HBV-specific antibodies. Differentiating or non-differentiating antigen or antibody determinations can in each case be carried out in one assay mixture.

Finally, the disclosure also relates, in some embodiments to the detection of the corresponding nucleic acids with the aid of so-called nucleic acid assays (e.g. polymerase chain reaction, PCR) with the aid of suitable primers, and to the use of the novel amino acid sequences for preparing vaccines.

Hepatitis B virus (HBV) is well known to induce disorders with a multiplicity of courses, from infections with mild, inapparent courses to chronically active inflammations of the liver (viral hepatitis) having fulminant courses.

Chronic infection with HBV represents a global health problem, with 400 million people estimated to be affected (Lee, N. Engl. J. Med. 337; 1733-1745 (1997)).

The most suitable prophylactic measures for HBV infection, which is to be encountered frequently around the world, are regarded as being active immunization (stimulation of the antibody response through administration of antigen) and also passive immunization (by injection of preformed antibodies).

HBV is one of the hepadna viruses and takes the form of a virus particle with a diameter of 42 nm consisting of core and envelope. The genome of the virus is a partially double-stranded, circular DNA sequence of about 3200 nucleotides which encode at least six different viral genes (Tiollais et al., Nature 317: 489-495 (1985)). Four open reading frames are present for forming the viral proteins.

The S gene contains the information for the HBV surface antigen (HBsAg) which is also called small protein (S). There are in addition larger forms which are referred to as large protein (L) and middle protein (M). The S-HBsAg sequence which comprises 226 amino acids is common to all three proteins (Gerlich et al., Viral Hepatitis and Liver Disease, Hollinger et al., William-Wilkens, Baltimore, Md., pages 121-134 (1991)).

The protein regions in front of the small HBs are also referred to as pre-S1 and pre-S2. The pre-S1 domain comprises, depending on the genotype, 108 or 119 amino acids, whereas the pre-S2 domain consists of 55 amino acids. Both domains are present in the L protein (389 or 400 amino acids, depending on genotype), whereas the M protein comprises only the pre-S2 together with the S antigen (281 amino acids). The pre-S proteins have different degrees of glycosilation and carry the receptors for recognizing liver cells.

The C gene carries the information for the nucleocapsid protein, hepatitis B core antigen (HBcAg). Translation of this protein may start even in the pre-C region and lead to the formation of hepatitis B e antigen (HBeAg). HBeAg differs in folding and immunogenicity from HBcAg. HBeAg, in contrast to HBcAg, occurs unbound in the serum and, if positively detected, is regarded as an indicator of the formation of HBcAg and thus of the formation of infectious viral particles.

The reverse transcription DNA polymerase present in the viral particle is encoded by the P gene, and it is suggested that the transactivator X gene is involved in causing the development of HBV-associated primary hepatocellular carcinomas.

The viral replication cycle of HBV includes an intracellular pre-genomic RNA which is transcribed into DNA in the viral nucleocapsid. Since the HBV-intrinsic reverse transcriptase DNA polymerase has no proof-reading capability, incorrect nucleotides are incorporated with relatively high frequency. As a consequence, the mutation rate of HBV, which is about 1 nucleotide/10 000 bases/infection year, is about 10 times that shown by other DNA viruses (Blum, Digestion 56: 85-95 (1995); Okamoto et al., Jpn. J. Exp. Med. 57: 231-236 (1987)). Deletions and insertions also occur rather frequently (Carman et al., Lancet 341: 349-353 (1993)).

The resulting variability of HBV is manifested inter alia in the occurrence of 9 serologically defined subtypes (Courouce et al., Bibliotheca Haematologica 42: 1 (1976)) and a total of at least 8 different genotypes which are referred to as A to H (FIG. 1) and show a geographic distribution. (Norder et al., J. Gen. Virol. 73: 3141-3145 (1992), Norder et al., Virology 198: 489-503 (1994), Norder et al., Intervirology 47: 289-309 (2004)). In addition, a number of mutants in which one amino acid or a plurality are exchanged, absent or supernumerary are described.

Besides naturally occurring mutations (Cooreman et al., Hepatology 30: 1287-1292 (1999)), administration of HBV immunoglobulins and/or antiviral therapy (e.g. with lamivudine) may exert a selection pressure which may lead to the increased occurrence of so-called escape mutants and distinctly increase the probability of the occurrence of HBV mutants (Terrault et al., Hepatology 28: 555-561 (1998); Tillmann et al., Hepatology 30: 244-256 (1999); Hunt et al., Hepatology 31: 1037-1044 (2000)).

Not all HBV mutations lead to viruses capable of replication, and there is often coexistence with virus capable of replication, thus limiting the accuracy of sequencing of isolated DNA or even leading to non-recognition of altered sequences by PCR, cloning operations with subsequent sequencing if these account quantitatively for <10% of the total DNA (Cooremann et al., J. Biomed. Sci. 8: 237-247 (2001)).

Accordingly, it is advantageous to isolate mutants, in which case the subsequent identification and characterization of individual mutants possibly leads to improved vaccines and/or diagnostic aids.

The immune response after HBV infection is mainly directed against the so-called a determinant as an S protein region which is common to all hepatitis B viruses and is located on the surface of the viral particles (Gerlich et al., supra) and which represent the most heterogeneous part of the B-cell epitopes of the S gene.

According to the current state of knowledge, a total of at least 5 partially overlapping epitopes on the a determinant between amino acid position 101 and 180 are assumed to be binding sites for antibodies (FIGS. 1 and 2), as it has been possible to show by using monoclonal antibodies (Peterson et al., J. Immunol. 132: 920-927 (1984)). These are mainly complex conformational epitopes stabilized by a plurality of disulfide bridges. There are also in some cases sequential epitopes which can be produced with the aid of synthetically prepared cyclic peptide structures.

So-called "protective antibodies" which circulate in the serum after a natural infection with HBV are 99% directed against the very immunogenic a determinant of HBV (Jilg, Vaccine 16: 65-68 (1998)). The wide application of immunization with vaccines which have either been isolated from human serum or prepared by genetic manipulation, and the administration of hepatitis B immunoglobulins which comprise human HBV-specific antibodies is based on this fact. Both prophylactic strategies are based on the neutralizing effect displayed by HBs-specific antibodies after binding to the "a-loop epitopes" (Carman et al., Hepatology 24: 489-493 (1996), Muller et al., J. Hepatol. 13: 90-96 (1991) and Samuel et al., N. Engl. J. Med. 329: 1842-1847 (1993)). Similarly, the diagnostic aids currently in wide use are based on the binding of a determinant-specific antibodies with epitopes of the a determinant. Thus, in the HBsAg determination used around the world in the blood-donation sector, HBV surface antigen circulating in the serum of donors is detected with immunochemical determination methods using antibodies against the a determinant (of polyclonal or monoclonal origin) and, if the result is positive, the corresponding blood donation is discarded in order to avoid iatrogenic HBV infections through HBV-contaminated blood. A further use of the HBsAg determination is in detecting the presence of an acute HBV infection.

Conversely, determination of HBs-specific antibodies in the blood of subjects is used to demonstrate, with a positive result of the determination of HBsAg-specific antibodies (anti-HBs) that either a natural infection has run its course or that a performed vaccination has taken place successfully.

Finally, nucleic acid testing for example with the aid of the polymerase chain reaction (PCR) is also based on the use of primers (starters) which are specific for HBV nucleotides.

Owing to the central role of the a determinant in active immunization (vaccination with HBV antigen), passive immunization (protection by HBV-specific immunoglobulins), demonstration of the success of vaccination or that an HBV infection has taken place (both by determining HBsAg-specific antibodies, anti-HBs) and finally safety in the blood-donation sector (HBsAg determination and PCR), it is understandable why great attention is paid in specialist circles to the occurrence of mutants and also novel variants, especially in the region of the a determinant.

Novel mutants and/or variants which have been altered in the a determinant of HBV but are capable of replication might anticipate both the prophylactic and the diagnostic concept (Brind et al., J. Hepatol. 26: 228-235 (1997), Fischer et al., Transplant Proc. 31: 492-493 (1999), Ghany et al., Hepatology 27: 213-222 (1998), Protzer-Knolle et al., Hepatology 27: 254-263 (1998), Carman et al., Gastroenterology 102: 711-719 (1992) and Coleman et al., WO 02/079217 A1, (2002)).

There is no sharp distinction between variants and mutants of HBV, but a proposal in this regard is widely used (Carman, J. Viral Hepat. 4 (suppl. 1): 11-20 (1997)). According to this, the term "variant" should be used for naturally occurring subtypes which occur without known interference, for example selection pressure through antiviral therapy and/or immunoglobulin administration, and exhibit a geographical distribution pattern.

The characterization and subsequent classification of subtypes takes place with the aid of monoclonal antibodies and is based on an altered reaction pattern owing to exchange of one or a few amino acid(s). Amino acid positions 122 or 160 of the most widespread HBV sequence: aa 122 and aa 160=lysine, K, represent the basis for the classification.

All serotypes comprise the group-specific a determinant, while aa 122 and additionally 133 and 134 determine the d and y subtypes and aa 160 determines the attribution to the w or r subtype. HBV subtypes can on this basis be roughly classified as adr, adw, ayr or ayw, which can be differentiated further into at least 9 sub-subtypes: ayw1, ayw2, ayw3, ayw4, ayr, adwr2, adw4, adrq+ and adrq− (Swenson et al., J. Virol. Meth. 33: 27-28 (1991), Blitz et al. J. Clin. Microbiol. 36: 648-651, Ashton-Rickardt et al., J. Med. Virol. 29: 204-214 (1989)).

Since this classification is based on a serological reactivity, it is not necessarily the case that each typing means a variability at the amino acid level, which is why genotyping at the S-gene level is preferred (Ohba et al., Virus Res. 39: 25-34 (1995)).

Subtypes occur in particular geographical and ethnic patterns, for as yet unknown reasons.

The term mutation should according to Carman be reserved for those variants which arise exclusively under selection pressure such as vaccination or antiviral therapy. Many mutations have already been described, some of which have led to diagnostically incorrect findings (Carman et al., Lancet 345: 1406-1407), and of which the aa exchanges mentioned below are quoted by way of example:

| Consensus: | aa Position | Mutant: |
|---|---|---|
| I | 110 | V |
| P | 111 | T |

-continued

| Consensus: | aa Position | Mutant: |
|---|---|---|
| T | 114 | S |
| T | 116 | S |
| P | 120 | T/S |
| T | 123 | A/N |
| I/T | 126 | A/S |
| Q | 129 | H/R |
| K/M | 133 | L |
| T | 143 | M/L |
| D | 144 | H/A/E |
| G | 145 | R/A |
| A | 157 | R and cysteine exchanges in aa positions 107, 124, 137, 147 & 149. |

(Coleman, supra; Okamoto et al., Pediatr. Res. 32: 264-268 (1992); Zhang et al., Scand. J. Infect. Dis. 28: 9-15 (1996); Zuckermann et al., Lancet 343: 737-738 (1994)).

Surprisingly, an atypical reaction pattern of hepatitis markers has been found in a sample (serum/plasma) of a patient suffering from liver inflammation in Berlin (internal identification number: 126734/305024817).

Besides the clinical presentation, an HBV infection is also indicated by detection of hepatitis B virus DNA, although it was not possible to detect HBsAg with an approved efficient HBsAg ELISA.

A sequencing which was carried out resulted completely surprisingly in the nucleotide sequence depicted in FIGS. 3 and 4 and the amino acid sequence depicted in FIGS. 5 and 6, both of which unexpectedly led to the described substitution pattern.

It is clear from these sequences that, entirely surprisingly, it is not a point mutation, i.e. exchange of a few nucleotides, which is involved, because a total of n=7 amino acids in the region from aa 100 to 181 have been replaced by comparison with the amino acid sequences of the representative geno types (FIG. 1). In view of the frequency of the amino acid replacements, it must surprisingly be assumed that a novel mutant is involved, or that the mutations are so pronounced that the consequence should rather be described as a novel variant, which is referred to hereinafter as HDB 07 variant.

Analysis of the best agreement of the amino acid sequence of the a determinant with known sequences indicates genotype D (FIG. 1), subtype ayw2 (FIG. 2), from which the novel variant however surprisingly differs in 8 aa positions (FIG. 6). The most prominent feature are the replacements at positions 122 and 160. Although the best agreement is achieved with genotype D, subtype ayw2, the amino acid at position 122 which determines the subtype is surprisingly replaced in relation to genotype D, subtype ayw2 (replacement of R by K), so that the subtype of the HDB-07 variant should correctly be referred to as ad. However, all subtype ad comparison sequences would lead to a poorer overall agreement as genotype D, subtype ayw2. It was completely surprising to find replacement of K by N at position 160. Since position 160 is decisive for attribution to the w subtype (K at position 160) or r subtype (R at position 160), the novel variant HDB-07 loses this subtype attribution through this replacement. Although loss of attribution to a subtype has been described as a very rare phenomenon in the literature (Okamoto et al., Mol. Immunol. 26(2): 197-205 (1989)), occurrence of such a phenotype together with a change of subtype caused by replacement is not as yet to be found in the literature.

Since it is known that epitopes on the a determinant are structurally related, that is may be in the form of so-called conformational epitopes, it is probable that the immunogenicity and also the binding ability of antibodies to the a determinant can be influenced by the amino acid exchange in position #100.

The present disclosure therefore relates to an oligo- or polypeptide comprising an amino acid sequence which has at least 92% identity with SEQ ID No: 5. The amino acid sequence shown in SEQ ID No: 5 corresponds to amino acid positions 100 to 180 of the S antigen of the hepatitis B virus, which antigen has a total length of 226 amino acid. Preferred embodiments relate to an oligo- or polypeptide comprising an amino acid sequence which has at least 93%, at least 94%, at least 95%, at least 96%, at least 97%, at least 98% or at least 99% identity with SEQ ID No: 5.

The present disclosure also relates, in some embodiments to an oligo- or polypeptide comprising an amino acid sequence which has at least 97.3% identity with SEQ ID No: 3. The amino acid sequence shown in SEQ ID No: 3 corresponds to the S antigen of the hepatitis B virus. Preferred embodiments relate to an oligo- or polypeptide comprising an amino acid sequence which has at least 97.6%, at least 97.9%, at least 98.2%, at least 98.5%, at least 98.8%, at least 99.1%, at least 99.4% or at least 99.7% identity with SEQ ID No: 3.

Determination of the identity between two amino acid sequences is known per se to the skilled worker and can be carried out with customary computer programs. Determination of identity is preferably carried out with the "Bestfit" computer program of the Genetics Computer Group (Madison, Wis.). The parameters are used in the standard settings (default). The version of the program current on the priority date of the present application is preferably used. A high percentage identity means a high correspondence, equality or equivalence of two sequences.

Some example embodiments of an oligo- or polypeptide of the disclosure may also comprise an amino acid sequence in which zero to seven amino acids in SEQ ID No: 5 are replaced, deleted or inserted. It is also possible for 0 to 6, 0 to 5, 0 to 4, 0 to 3, 0 to 2 amino acids or 1 amino acid in SEQ ID No: 5 to be replaced, deleted or inserted in the amino acid sequence. Replacements may also relate to the amino acid positions which correspond to positions 100, 105, 110, 118, 120, 142, 116 and 173 of the S antigen of HBV.

Some example embodiments of an oligo- or polypeptide of the disclosure may also comprise an amino acid sequence in which zero to six amino acids in SEQ ID No: 3 are replaced, deleted or inserted. It is also possible for 0 to 6, 0 to 5, 0 to 4, 0 to 3, 0 to 2 amino acids or 1 amino acid in SEQ ID No: 3 to be replaced, deleted or inserted in the amino acid sequence.

Some example embodiments of an oligo- or polypeptide of the disclosure may also comprise an amino acid sequence which is a partial sequence of SEQ ID No: 3 having at least 5 or at least 6 or at least 7 or at least 8 or at least 9 or at least 10 or at least 11 or at least 12 or at least 13 or at least 14 or at least 15 or at least 20 or at least 25 or at least 30 or at least 35 or at least 40 or at least 45 or at least 50 or at least 55 or at least 60 or at least 65 or at least 70 or at least 75 or at least 80 or at least 85 or at least 90 or at least 95 or at least 100 consecutive amino acids of SEQ ID No: 3, where this partial sequence includes at least one of positions 100, 105, 110, 118, 120, 142, 160 and 173 of SEQ ID No: 3.

The partial sequence preferably includes two, three, four, five, six, seven or all eight of positions 100, 105, 110, 118, 120, 142, 160 and 173 of SEQ ID No: 3.

Some example embodiments of a polypeptide of the disclosure may also comprise a fragment of an HBs antigen of a hepatitis B virus, where the fragment has a length of at least 5 or at least 6 or at least 7 or at least 8 or at least 9 or at least 10 or at least 11 or at least 12 or at least 13 or at least 14 or at least 15 amino acids, the HBs antigen has cysteine at position 100, arginine at position 105, leucine at position 110, arginine at position 118, leucine at position 120, leucine at position 142, asparagine at position 160 and proline at position 173, and the fragment comprises cysteine 100, arginine 105, arginine 118, leucine 120, leucine 142, asparagine 160 and/or proline 173. The oligo- or polypeptide may include one, two, three, four, five, six or seven of these specific amino acid residues.

The total length of oligo- or polypeptides of the disclosure is ordinarily from 5 to 1000 amino acids, preferably 6 to 500 amino acids, more preferably 7 to 300 amino acids, most preferably 8 to 200 amino acids according to some embodiments of the disclosure. The oligo- or polypeptides may also comprise foreign amino acids which are not encoded by the genome of a hepatitis B virus. Thus, amino acids which facilitate coupling to solid phases or which make coupling to labeling substances possible may be present. Amino acids which result from the cloning and have also been expressed in the recombinant expression may be present. Finally, some example embodiments of an oligo- or polypeptide of the disclosure may be a fusion protein which, besides amino acids derived from HBV, comprises a fusion partner, e.g. a “tag” sequence which facilitates purification, or a protein portion which increases the solubility and/or yield on recombinant expression. Fusion partners of these types are known per se to the skilled worker.

In another embodiment, the oligo- or polypeptides contain no foreign amino acids not encoded by the genome of an HBV. Accordingly, these oligo- or polypeptides consist of one of the amino acid sequences described above and/or in the claims.

Some example embodiments of an oligo- or polypeptide of the disclosure are preferably immunogenic, i.e. it can induce an antibody response in a mammalian organism. The oligo- or polypeptide normally comprises at least one antigenic determinant or at least one epitope. In a particular embodiment, the oligo- or polypeptide comprises an epitope which is not present in other HBV variants, e.g. in the subtype ayw2.

The oligo- or polypeptide preferably comprises one of the amino acid sequences SEQ ID No: 3, SEQ ID No: 4 and SEQ ID No: 5.

A further aspect of the disclosure, according to some embodiments, is an immunogenic peptide or a mixture of immunogenic peptides comprising one or more of the oligo- or polypeptides described in this application. The immunogenic peptide or the immunogenic mixture may comprise the oligo- or polypeptide(s) alone or in combination with known HBV immunogens.

The present disclosure also relates, in some embodiments, to nucleic acid molecules which are derived from the genome of the novel HBV variant HDB 07 or mutants thereof, especially nucleic acid molecules derived from the gene which encodes HBsAg.

The disclosure therefore relates for example to an oligo- or polynucleotide which comprises a nucleotide sequence which has at least 95.86% identity with SEQ ID No: 2. The nucleotide sequence SEQ ID No: 2 codes for an amino acid sequence SEQ ID No: 5. Preferred embodiments relate to an oligo- or polynucleotide comprising a nucleotide sequence which has at least 95.8%, at least 96.4%, at least 97.0%, at least 97.6%, at least 98.2%, at least 98.8%, or at least 99.4% identity with SEQ ID No: 2.

The disclosure also relates, in some embodiments, to an oligo- or polynucleotide comprising a nucleotide sequence which has at least 98.5%, at least 98.8%, at least 99.1%, at least 99.4% or at least 99.7% identical to SEQ ID No: 1. The nucleotide sequence SEQ ID No: 1 codes for the amino acid sequence SEQ ID No: 3.

Identity is defined herein as the degree of equality between two strands of two DNA segments. The identity is expressed as a percentage by dividing the number of identical bases of two sequences to be compared by the length of the shorter sequence and multiplying by 100 (Smith et al., Adv. Appl. Mathem. 2: 482-489 (1981)).

Determination of the identity between two amino acid sequences is known per se to the skilled worker and can be carried out with customary computer programs. The identity is preferably determined using the “Bestfit” computer program of the Genetics Computer Group (Madison, Wis.). The parameters are used in the standard settings (default). The version of the program current on the priority date of the present application is preferably used. A high percentage identity means a high correspondence, equality or equivalence of two sequences.

This assessment can also be applied to amino acid sequences of peptides and proteins (Dayhoff; Atlas of Protein Sequences and Structure, M. O. Dayhoff ed. 5 Suppl. 3: 353-358, Nat. Biom. Res. Found., Washington D.C., USA, Gribskov, Nucl. Acids Res. 14 (6): 6745-66763 (1986)).

The disclosure further relates, in some embodiments, to an oligo- or polynucleotide comprising a nucleotide sequence in which zero to 10 nucleotides are replaced, deleted or added by comparison with SEQ ID No: 2. It is also possible for 0 to 9, 0 to 8, 0 to 7, 0 to 6, 0 to 5, 0 to 4, 0 to 3, 0 to 2 nucleotides or 1 nucleotide in SEQ ID No: 2 to be replaced, deleted or inserted in the nucleotide sequence.

Some example embodiments of an oligo- or polynucleotide of the disclosure may also comprise a nucleotide sequence which is a partial sequence of SEQ ID No: 1 having at least 8 consecutive nucleotides of SEQ ID No: 1, where the partial sequence includes at least one of positions 298, 299, 300, 310, 311, 312, 313, 314, 315, 328, 329, 330, 343, 344, 345, 352, 353, 354, 358, 359, 360, 364, 365, 366, 424, 425, 426, 478, 479, 480, 517, 518 and 519 of SEQ ID No: 1. The partial sequence preferably comprises at least 9, more preferably at least 10, yet more preferably at least 11, most preferably at least 12 consecutive nucleotides of the nucleotide sequence shown in SEQ ID No: 1. In further embodiments, the partial sequence comprises at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, at least 50, at least 60, at least 70, at least 80, at least 90, at least 100, at least 120, at least 150, at least 175, at least 200, at least 250, or at least 300 consecutive nucleotides of the nucleotide sequence shown in SEQ ID No: 1.

The partial sequence preferably includes two, three, four, five, six, seven, eight, nine, ten, eleven, twelve, 13, 14, 15, 16, 17, 18, 19, 20, 21, 22, 23, 24, 25, 26, 27, 28, 29 or all 30 of positions 298, 299, 300, 310, 311, 312, 313, 314, 315, 328, 329, 330, 343, 344, 345, 352, 353, 354, 358, 359, 360, 364, 365, 366, 424, 425, 426, 478, 479, 480, 517, 518 and 519 of SEQ ID No: 1.

In another embodiment, the oligo- or polynucleotide comprises a nucleotide sequence which hybridizes under stringent conditions, preferably specifically, with a polynucleotide complementary to the sequence SEQ ID No: 1 or to SEQ ID No: 2. Methods for determining whether a given oligo- or polynucleotide hybridizes with another polynucleotide are known per se to the skilled worker. A specific example of “stringent conditions” are the following conditions: a) incubation at 42° C. for 16 hours in a solution comprising 50% formamide, 5×SSC (150 mM NaCl, 15 mM trisodium citrate), 50 mM sodium phosphate pH 7.6, 5×Denhardt's solution, 10% dextran sulfate and 20 μg/ml denatured, sheared salmon sperm DNA; b) subsequent washing in 0.1×SSC at approximately 65° C. Hybridization and washing conditions are known per se to the skilled worker and indicated by way of example in Sambrook et al., Molecular Cloning: A Laboratory Manual, Second Edition, Cold Spring Harbor, N.Y., (1989). A nucleotide sequence hybridizes specifically onto a given polynucleotide if it hybridizes substantially more weakly or not at all onto other nucleotide sequences. In the present case this may mean that the nucleotide sequence hybridizes only weakly or not at all onto HBsAg-encoding polynucleotides from conventional HBV variants (e.g. genotype D, subtype ayw2).

The disclosure also relates, in some embodiments, to an oligo- or polynucleotide comprising a nucleotide sequence which codes for an oligo- or polypeptide as described herein. A further aspect of the disclosure is an oligo- or polynucleotide comprising a nucleotide sequence complementary to the nucleotide sequences described above.

The minimum length of the oligo- or polynucleotides of the disclosure is 6, preferably 8, more preferably 10, most preferably 12 nucleotides, according to some embodiments. The total length of the oligo- or polynucleotide is ordinarily from 6 to 3000 nucleotides, preferably 6 to 1500 nucleotides, more preferably 8 to 900 nucleotides, most preferably 8 to 600 nucleotides. The oligo- or polynucleotides may also comprise nucleotides which are not derived from the genome of a hepatitis B virus. Thus, nucleotides which code for particular amino acids which are intended to carry out desired functions as described above may be present. Nucleotides resulting from the cloning, e.g. in order to introduce particular cleavage sites, may be present. Finally, some example embodiments of an oligo- or polynucleotide of the disclosure may code for a fusion protein which, besides amino acids derived from HBV, comprises a fusion partner, e.g. a "tag" sequence which facilitates purification, or a protein portion which increases the solubility and/or yield on recombinant expression. Fusion partners of these types and the DNA encoding them are known per se to the skilled worker.

Preferred oligo- or polynucleotides, according to some embodiments of the present disclosurecomprise a nucleotide sequence which is selected from the group consisting of SEQ ID No: 1 and SEQ ID No: 2.

Polynucleotides of the disclosure may also be labeled, for example by a fluorescent label or radioactive label. Polynucleotides of these types can advantageously be employed in a hybridization reaction or a polymerase chain reaction (PCR).

The disclosure also relates, in some embodiments, to a vector or a plasmid comprising an oligo- or polynucleotide according to the present disclosure. The plasmid may be for example a cloning vector which serves to replicate the nucleic acid in host cells or to provide certain restriction cleavage sites. Expression vectors are vectors which allow expression of the cloned nucleic acid in host cells. Host cells may be various prokaryotic or eukaryotic cells. Prokaryotic host cells are for example bacterial cells such as *E. coli* cells. Some example embodiments of expression vectors of the disclosure may comprise certain control elements such as, for example, promoters or binding sites for repression factors. In a further embodiment, the expression vectors comprise a nucleic acid segment which codes for a part of a fusion protein.

The disclosure likewise relates to a cell, e.g. a host cell, which comprises a polynucleotide, plasmid or vector of the disclosure. The host cells can be cultured under suitable conditions such that transcription of the contained nucleic acid and subsequent translation takes place. The disclosure also relates, in some embodiments, to a method for preparing a polypeptide in which a polynucleotide, a plasmid or an expression vector of the disclosure is introduced into host cells, and the host cells are cultured under conditions which lead to expression of the polypeptide. The polypeptide can subsequently be obtained from the host cells where appropriate. The preparation of the polypeptide preferably takes place in bacteria, most preferably in *E. coli* cells. Suitable means and conditions for culturing are described for example in Ausubel et al. (1993) "Current Protocols in Molecular Biology". The expressed polypeptide is obtained by methods known per se to the skilled worker. Various methods for protein purification are described for example in Scopes R. (1994) "Protein Purification: Principles and Practice" ($3^{rd}$ edition) Springer Verlag.

In some embodiments, polypeptides and peptides of the present disclosure can, however, also be prepared chemically by known methods such as, for example, solid-phase synthesis. It is likewise possible for the polynucleotides of the disclosure to be prepared by known methods of chemical synthesis. Polynucleotide fragments obtained by chemical synthesis can then also be linked enzymatically by ligases. The oligo- or polynucleotides of the disclosure can also be prepared by site-directed mutagenesis from known sequences, by introducing point mutations at particular positions. Methods of these types are known per se to the skilled worker.

A further aspect of the disclosure is an antibody which, according to some embodiments, binds to an oligo- or polypeptide of the disclosure. Such antibodies can be prepared in a known manner, either by means of an oligo- or polypeptide of the disclosure, e.g. a peptide having one of the sequences SEQ ID No: 12 to 30, or a fragment thereof (Harlow and Lane (1988) Antibodies: A Laboratory Manual; Cold Spring Harbor Laboratory). It is possible for the antibodies to be polyclonal or monoclonal, but monoclonal antibodies are preferred. The antibodies are preferably specifically directed against the HBsAg of the novel HBV variant, but do not recognize HBsAg from other HBV variants, e.g. genotype D subtype ayw2. Such antibodies can be obtained by identifying, by means of a sequence comparison of the amino acid sequences of the novel HBsAg and HBsAg from known strains, peptides which are specific for the novel HBsAg, and using these peptides to prepare the antibodies. It is also possible to prepare a mixture of polyclonal antibodies and deplete them by incubation with known HBsAg. In another embodiment, the antibody recognizes not only the novel HBsAg but also known HBsAg variants. It is possible thereby to detect different variants of HBsAg simultaneously.

Some example embodiments of an antibody of the disclosure can bind to an oligo- or polypeptide which consists of an amino acid sequence which is selected from the group consisting of SEQ ID No: 3, SEQ ID No: 4, SEQ ID No: 5, SEQ ID No: 6, SEQ ID No: 7, SEQ ID No: 8, SEQ ID No: 9, SEQ ID No: 10, SEQ ID No: 11, SEQ ID No: 12, SEQ ID No: 13, SEQ ID No: 14, SEQ ID No: 15, SEQ ID No: 16 and SEQ ID No: 17. The antibody particularly preferably binds to an oligo- or polypeptide which consists of an amino acid sequence which is selected from the group consisting of SEQ ID No: 6, SEQ ID No: 7, SEQ ID No: 8, SEQ ID No: 9, SEQ ID No: 10, SEQ ID No: 11, SEQ ID No: 12, SEQ ID No: 13, SEQ ID No: 14, SEQ ID No: 15, SEQ ID No: 16 and SEQ ID No: 17. In a particular embodiment, the antibody does not bind to the a determinants of the known HBV genotypes A, B, C, D, E and F (see FIG. 1). In a particular embodiment, the antibody does not bind to the a determinant of HBV genotype D, subtype ayw2.

The disclosure also relates, in some embodiments, to antibodies which react with the a determinant described in SEQ ID No: 11 to 22, in which case the binding preferably takes place in the amino acid region aa 100 to 107, aa 117 to 123, aa 156 to 166, or aa 168 to 178. The antibodies may be polyclonal or monoclonal of animal or human origin.

The disclosure further relates, in some embodiments, to an anti-idiotype antibody which represents an amino acid sequence of an oligo- or polypeptide of the disclosure. Methods for preparing anti-idiotype antibodies are known per se to the skilled worker.

The disclosure also relates, in some embodiments, to an assay kit for detecting hepatitis B viruses, comprising an oligo- or polypeptide of the disclosure, an oligo- or polynucleotide of the disclosure and/or an antibody of the disclosure.

The disclosure also relates, in some embodiments, to an immunogenic peptide or a mixture of immunogenic peptides, comprising one or more of the oligo- or polypeptides of the disclosure, alone or in combination with known HBV immunogens.

A further aspect of the disclosure, according to some embodiments, is a method for detecting a hepatitis B antigen, which comprises (a) incubating a sample with an antibody of the disclosure under conditions which allow the formation of an antigen-antibody complex; and (b) detecting an antigen-antibody complex which comprises the antibody.

It is possible to use monoclonal or polyclonal antibodies (or mixtures or fragments thereof or mixtures of fragments) which react with epitopes of the novel HBV variant in order to determine the a determinant of the HBV variant of the disclosure in the form of the complete polypeptide sequence or parts thereof in investigation samples: HBsAg of the HDB 07 variant.

The skilled worker is familiar with a large number of determination methods in which immune complexes are formed, or the formation thereof is inhibited, with one or more monoclonal antibody(s) or polyclonal antibodies (or mixtures thereof or fragments or mixtures of fragments) which are specific for the a determinant of the HBV variant.

A specific embodiment is represented by the so-called enzyme immunoassay, of which a possible assay principle is described by way of example below, but without restricting the concept of the disclosure thereto:

In the very widely used so-called sandwich principle, antibodies or fragments thereof immobilized on a suitable support (e.g. microparticles or surface of wells of a microtitration plate) are incubated with the investigation sample. HBsAg bound to the antibodies is detected after removal of excess sample, by further incubation with anti-HBs antibodies (monoclonal or polyclonal or fragments or mixtures of these fragments) which are provided with a probe. The probe frequently employed is an enzyme whose catalytic conversion (after removal of the excess reagent) of a suitable substrate leads to a color reaction which is measured by photometry and whose intensity is proportional to the HBsAg content present in the sample.

Besides this specific embodiment, methods which are homogeneous in nature are also known (i.e. do not require bound/free separation) and make do entirely without a probe (e.g. agglutination methods), can be evaluated with the naked eye (e.g. radial immunodiffusion) or make use of other probes (e.g. radioactive isotopes or chemiluminescence) or a plurality of probes (such as, for example, the biotin/streptavidin system).

One of ordinary skill in the art who has the benefit of the present disclosure will recognize that "determination of HBsAg of the novel HBV variant" with the present disclosure means all methods suitable for detecting polypeptide sequences or antigens of the novel HBV variant may be used, irrespective of whether the HBsAg of the novel variant is determined alone or in conjunction with HBsAg of known a determinants and/or known mutations in the a region.

It is likewise possible to combine, for economic reasons, an HBsAg determination with a detection method for a further analyte (e.g. HIV antigen or simultaneous determination of HBV variant HBsAg and specific antibodies directed against it) in one assay mixture (differentiating or non-differentiating).

The disclosure also relates, in some embodiments, to a method for detecting antibodies directed against a hepatitis B virus antigen, which comprises (a) incubating a sample with an oligo- or polypeptide under conditions which allow formation of an antigen-antibody complex; and (b) detecting the antibody-antigen complex which comprises the oligo- or polypeptide.

A specific embodiment is represented by the so-called enzyme immunoassay, of which a possible assay principle is described by way of example below, but without restricting the concept of the disclosure thereto:

In the very widely used so-called sandwich principle, epitope-carrying polypeptide or protein sequences immobilized on a suitable support (e.g. microparticles or surface of wells of a microtitration plate) are incubated with the investigation sample. Antibodies bound to the epitopes are detected after removal of excess sample, by a further incubation with epitope-carrying polypeptide or protein sequences which are provided with a probe. A probe frequently employed is an enzyme whose catalytic conversion (after removal of the excess reagent) of a suitable substrate leads to a color reaction which is measured by photometry and whose intensity is proportional to the antibody content present in the sample.

Besides this specific embodiment, methods which are homogeneous in nature are also known (i.e. do not require bound/free separation) and make do entirely without a probe (e.g. agglutination methods), can be evaluated with the naked eye (e.g. radial immunodiffusion) or make use of other probes (e.g. radioactive isotopes or chemiluminescence) or a plurality of probes (such as, for example, the biotin/streptavidin system).

Likewise, the polypeptide structures of the HBV variant can be represented by anti-idiotype antibodies or, by choosing a suitable assay principle, variant-specific monoclonal or polyclonal antibodies can also be used to determine anti-HBs antibodies (e.g. in a competitive assay format). It is likewise known that differentiation of the immunoglobulin classes is also possible by choosing the assay principle (e.g. by the "indirect" method with a second class-specific antibody (e.g. IgG or IgM specific) with probe or with the aid of the so-called anti-μ principle (IgM specific). It is of course necessary for the methods and materials (including probe and polypeptide sequences) to be adapted to the particular target.

One of ordinary skill in the art who has the benefit of the present disclosure will recognize that "determination of antibodies which are specific for the a determinant of the novel HDB 07 variant" means all methods suitable for detecting immunoglobulins and/or immunoglobulin classes against the novel HBV variant, irrespective of whether the antibody against the novel variant is sought alone or in conjunction with antibodies against known a determinants and/or known mutations in the a region may be used.

It is possible in another method to detect a hepatitis B nucleic acid. This method comprises (a) incubating a sample with an oligo- or polynucleotide of the disclosure under conditions which allow selective hybridization of the oligo- or polynucleotide with a hepatitis B nucleic acid in the sample; and (b) determining whether polynucleotide duplexes which include the oligo- or polynucleotide have been formed.

The hepatitis B nucleic acid can also be detected by (a) incubating a sample with at least one oligo- or polynucleotide of the disclosure under conditions which allow selective hybridization of the oligo- or polynucleotide with a hepatitis B nucleic acid in the sample; (b) carrying out a polymerase chain reaction; and (c) determining whether a nucleic acid has been amplified.

The disclosure also relates, in some embodiments, to the use of an oligo- or polynucleotide of the disclosure as primer and/or as probe. The present nucleotide sequences can be used to prepare primers and/or gene probes, which, according to some embodiments, may be included is why the disclosure likewise relates to kits comprising primers and/or probes for detecting HBV variant-specific nucleic acid either alone or in conjunction with known HBV nucleotide sequences in investigation samples.

It is possible on the basis of the present nucleotide sequences to develop primers which are used in the so-called polymerase chain reaction (PCR). PCR is a method for amplifying a desired nucleotide sequence of a nucleic acid or of a nucleic acid mixture. This entails the primers being in each case specifically extended by a polymerase with the desired nucleic acid as reading frame. After dissociation from the original strand, new primers are hybridized and again extended by the polymerase. Repetition of these cycles achieves enrichment of the target sequence molecules sought.

In relation to nucleic acid assays (NAA) it is possible to use nucleotide sequences of the present disclosure in order to prepare DNA oligomers of 6-8 nucleotides or larger which are suitable as hybridization probes for detecting the viral genome of the HBV variant described herein in people possibly carrying the virus variant, or for example in the blood-donation sector to screen stored blood for the presence of the variant genome either specifically or in combination with detection of nucleotide sequences of known HBV variants and/or HBV mutants.

It is likewise possible on the basis of the found nucleotide sequences of the novel HBV variant to develop appropriate primers which are specific for the novel variant or are able to detect both the novel variant and variants known in the prior art.

The present disclosure further relates to an isolated hepatitis B virus which includes an HBs antigen which comprises an amino acid sequence having at least 92% identity with SEQ ID No: 5. The HBs antigen of the virus of the disclosure preferably comprises the amino acid sequence SEQ ID No: 5. Finally, the disclosure also includes cultures of tissue cells which are infected with an HBV variant of the disclosure, as well as an isolated HBV variant itself. The disclosure also relates, in some embodiments, to an immunogenic preparation which comprises the attenuated or inactivated HDB 07 variant of HBV.

The disclosure likewise relates, in some embodiments, to an isolated HBV variant, where the virus has an a determinant in which aa 160 is not K or R, and aa 122 does not correspond to the consensus of the genotype with the best agreement.

The disclosure also relates, in some embodiments, to the use of an oligo- or polynucleotide of the disclosure or of an oligo- or polypeptide of the disclosure for manufacturing a medicament for the treatment or prevention of an HBV infection. The oligo- or polynucleotides or oligo- or polypeptides of the disclosure can be used in particular for producing a vaccine against HBV.

The disclosure also includes, according to some embodiments, a vaccine comprising a polypeptide of the present disclosure and a conventional adjuvant (e.g. Freund's adjuvant, phosphate-buffered saline or the like). A vaccine of this type can be used to induce the formation of antibodies in mammals. Similarly, the disclosure includes a particle which comprises a non-variant-specific amino acid sequence which induces particle formation together with an epitope-containing polypeptide which is specific for an HBV variant of the disclosure.

The nucleotide sequences of the disclosure can also be used to produce so-called antisense oligonucleotides (where appropriate for therapeutic purposes).

The present application further relates to the following aspects (1) to (21):

(1) an isolated oligo- or polynucleotide having one of the sequences selected from the group of SEQ ID No: 1 to SEQ ID No: 2 and SEQ ID No: 18 to SEQ ID No: 27:

```
SEQ ID No: 1
1 ATGGAGAACATCACATCAGGATTCCTAGGACCCCTGCTGTGTTACAGGCGGGGTTTTTC

  TTGTTGACAAGAATCCTCACAATACCGCAGAGTCTAGACTCGTGGTGGACTTCTCTCAAT

  TTTCTAGGGGGAACTACCGTGTGTCTTGGCCAAAATTCGCAGTCCCCAACCTCCAATCAC

  TCACCAACCTCCTGTCCTCCAACTTGTCCTGGTTATCGCTGGATGTGTCTGCGGCGTTTT

  ATCATCTTCCTCTTCATCCTGCTGCTATGCCTCATCTTCTTGTTGGTTCTTCTGGACTGT

  CAAGGTATGTTACGCGTTTGTCCTCTACTTCCAGGATCTTCAACCACCAGCAGGGGACTA

  TGCAAAACCTGCACGACTCCTGCTCAAGGAACCTCTATGTATCCCTCCTGTTGCTGTACC

  AAACTTTCGGACGGAAATTGCACCTGTATTCCCATCCCATCATCCTGGGCTTTCGGAAAC

  TTCCTATGGGAGTGGGCCTCAGCCCGTTTCTCCTGGCCCAGTTTACTAGTGCCATTTGTT

  CAGTGGTTCGTAGGGCTTTCCCCCACTGTTTGGCTTTCAGTTATATGGATGATGTGGTAT

  TGGGGGCCAAGTCTGTACAGCATCTTGAGTCCCTTTTTACCGCTGTTACCAATTTTCTTT

  TGTCTTTGGGTATACATT  678
```

-continued

SEQ ID No: 2
1 TGTCAAGGTATGTTACGCGTTTGTCCTCTACTTCCAGGATCTTCAACCACCAGCAGGGGA

CTATGCAAAACCTGCACGACTCCTGCTCAAGGAACCTCTATGTATCCCTCCTGTTGCTGT

ACCAAACTTTCGGACGGAAATTGCACCTGTATTCCCATCCCATCATCCTGGGCTTTCGGA

AACTTCCTATGGGAGTGGGCCTCAGCCCGTTTCTCCTGGCCCAGTTTACTAGTGCCATTT

GTT 242

SEQ ID No: 18
AGCAGGGGACTA

SEQ ID No: 19
AGCAGGGGACTATGCAAA

SEQ ID No: 20
AGCAGGGGACTATGCAAAACCTGC

SEQ ID No: 21
AGCAGGGGACTATGCAAAACCTGCACGACTCCTGCTCAAGGAACC

SEQ ID No: 22
AGCAGGGGACTATGCAAAACCTGCACGACTCCTGCTCAAGGAACCTCTATGTATCCCTCCTG

TTGCTGTACCAAACTTTCG

SEQ ID No: 23
TTCGGAAACTTC

SEQ ID No: 24
TGGGCTTTCGGAAACTTC

SEQ ID No: 25
CCATCATCCTGGGCTTTCGGAAACTTC

SEQ ID No: 26
AATTGCACCTGTATTCCCATCCCATCATCCTGGGCTTTCGGAAACTTC

SEQ ID No: 27
CCCTCCTGTTGCTGTACCAAACTTTCGGACGGAAATTGCACCTGTATTCCCATCCCATCATC

CTGGGCTTTCGGAAACTTC (2) an oligo- or polynucleotide according to (1) which is in each case at least 65% or 66% or 67% or 68% or 69% or 70% or 71% or 72% or 73% or 74% or 75% or 76% or 77% or 78% or 79% or 80% or 81% or 82% or 83% or 84% or 85% or 86% or 87% or 88% or 89% or 90% or 91% or 92% or 93% or 94% or 95% or 99% or 97% or 98% or 99% identical to one of the sequences selected from the group of SEQ ID No: 1 to SEQ ID No: 2 or selected from the group of SEQ ID No: 18 to SEQ ID No: 27.

(3) an oligo- or polynucleotide according to (1) or (2) which hybridizes under stringent conditions with an oligo- or polynucleotide which has a sequence complementary to one of the sequences selected from the group of SEQ ID No: 1 to SEQ ID No: 2 or selected from the group of SEQ ID No: 18 to SEQ ID No: 27.

(4) an isolated oligo- or polynucleotide which codes for HBs antigen of the hepatitis B virus and comprises an oligo- or polynucleotide according to (1), (2) or (3).

(5) a fragment of an oligo- or polynucleotide which codes for HBs antigen of the hepatitis B virus, wherein the fragment comprises an oligo- or polypeptide according to (1), (2) or (3).

(6) an isolated oligo- or polynucleotide which codes for the a determinant of the HBs antigen of the hepatitis B virus and comprises an oligo- or polynucleotide according to (1), (2) or (3).

(7) a primer which is specific for an oligo- or polynucleotide according to any of aspects (1) to (6).

(8) a vector which comprises at least one oligo- or polynucleotide according to any of aspects (1) to (5).

(9) a host cell which comprises a vector according to (8).

(10) an oligo- or polypeptide which is encoded by an oligo- or polynucleotide according to any of aspects (1) to (5).

(11) isolated oligo- or polypeptide which has an amino acid sequence selected from the group of SEQ ID No: 3 to SEQ ID No: 17:

SEQ ID No: 3
1 M E N I T S G F L G P L L V L Q A G F F

L L T R I L T I P Q S L D S W W T S L N

F L G G T T V C L G Q N S Q S P T S N H

S P T S C P P T C P G Y R W M C L R R F

I I F L F I L L L C L I F L L V L L D C

Q G M L R V C P L L P G S S T T S R G L

C K T C T T P A Q G T S M Y P S C C C T

K L S D G N C T C I P I P S S W A F G N

F L W E W A S A R F S W P S L L V P F V

Q W F V G L S P T V W L S V I W M M W Y

W G P S L Y S I L S P F L P L L P I F F

C L W V Y I 226

-continued

```
SEQ ID No: 4
1 C Q G M L R V C P L L P G S S T T S R G

  L C K T C T T P A Q G T S M Y P S C C C

  T K L S D G N C T C I P I P S S W A F G

  N F L W E W A S A R F S W P S L L V P F

  V Q W F V G L S P T V  91

SEQ ID No: 5
1 C Q G M L R V C P L L P G S S T T S R G

  L C K T C T T P A Q G T S M Y P S C C C

  T K L S D G N C T C I P I P S S W A F G

  N F L W E W A S A R F S W P S L L V P F

  V  81

SEQ ID No: 6
S T T S R

SEQ ID No: 7
T T S R G

SEQ ID No: 8
T S R G L

SEQ ID No: 9
S R G L C

SEQ ID No: 10
R G L C K

SEQ ID No: 11
G L C K T

SEQ ID No: 12
L C K T C

SEQ ID No: 13
W A F G N

SEQ ID No: 14
A F G N F

SEQ ID No: 15
F G N F L

SEQ ID No: 16
G N F L W

SEQ ID No: 17
N F L W E
```

(12) oligo- or polypeptide according to (10) or (11) which is in each case at least 65% or 66% or 67% or 68% or 69% or 70% or 71% or 72% or 73% or 74% or 75% or 76% or 77% or 78% or 79% or 80% or 81% or 82% or 83% or 84% or 85% or 86% or 87% or 88% or 89% or 90% or 91% or 92% or 93% or 94% or 95% or 99% or 97% or 98% or 99% identical to one of the sequences selected from the group of SEQ ID No: 3 to SEQ ID No: 17.

(13) isolated polypeptide corresponding to the sequence of the HBs antigen of the hepatitis B virus, which comprises an oligo- or polypeptide according to any of aspects (10) to (12).

(14) fragment of a polypeptide which corresponds to the sequence of the HBs antigen of the hepatitis B virus, which fragment comprises an oligo- or polypeptide according to any of aspects (10) to (12).

(15) isolated polypeptide which codes for the a determinant of the HBs antigen of the hepatitis B virus, which comprises an oligo- or polypeptide according to any of aspects (10) to (12).

(16) monoclonal or polyclonal antibody which binds to HBs antigen comprising an oligo- or polypeptide according to any of aspects (10) to (15), but which binds at least significantly more weakly or not at all to HBs antigen of a hepatitis B wild-type virus.

(17) an anti-idiotype antibody which represents an amino acid sequence according to any of aspects (10) to (15).

(18) assay kit for the detection or the determination by means of a hybridization reaction of a nucleic acid which is specific for a variant or mutant of the hepatitis B virus, using at least one oligo- or polynucleotide according to one or more of aspects (1) to (7).

(19) assay kit for the immunochemical detection or the immunochemical determination of an antigen which is specific for a variant or mutant of the hepatitis B virus, using at least one monoclonal or polyclonal antibody according to (16).

(20) assay kit for the immunochemical detection or the immunochemical determination of an antibody directed against a variant or mutant of the hepatitis B virus, using at least one oligo- or polypeptide according to any of aspects (10) to (15).

(21) immunogenic peptide or mixture of immunogenic peptides comprising one or more oligo- or polypeptides according to one or more of aspects (3) and (4) alone or in combination with known HBV immunogens.

The present disclosure includes, according to some embodiments, an isolated nucleotide sequence which is at least 65% identical to SEQ ID No: 1, or to a fragment of this sequence depicted in FIGS. 3 and 4, which fragment specifically hybridizes with the complement of SEQ ID No: 1 to 2 or SEQ ID No: 18 to 27.

The present disclosure additionally comprises, in some embodiments, an isolated nucleotide sequence which encodes the present variant according to the disclosure of the a determinant of the hepatitis B surface antigen (HBsAg) in the amino acid positions between aa 1 and 226, or leads to a peptide product which agrees at least 65% in the aa sequence with the SEQ ID No: 3 depicted in FIG. 5 or with the SEQ ID No: 4 depicted in FIG. 6, or fragments thereof according to SEQ ID No: 5 to 17.

The present disclosure further relates, according to some embodiments, to a vector comprising one or more of said nucleotide sequences, as well as a host cell which comprises this vector and a method for preparing a corresponding polypeptide from the a determinant, comprising incubating the abovementioned host cell over times and under conditions necessary for expression of the polypeptide.

The disclosure also relates, in some embodiments, to antibodies which react with the a determinant described in SEQ ID No: 3 to 17, where the binding preferably takes place in the amino acid region aa 100 to 180. The antibodies may be polyclonal or monoclonal of animal or human origin.

The disclosure likewise relates, according to some embodiments, to an isolated HBV variant, where the virus includes an a determinant which corresponds to the aa sequences at least between approximately position 100 and 160.

The present disclosure also relates, in some embodiments, to an immunogenic mixture for generating polyclonal or monoclonal antibodies, comprising the described isolated HBV or one or more of the described polypeptides.

The disclosure also relates, according to some embodiments, a polynucleotide probe comprising an HBV genome sequence which leads by replacement of amino acids to a modified a determinant which is identical or corresponds at least 65% with the described aa sequence of the novel HBV variant.

The disclosure likewise also relates, in some embodiments, to kits for detecting polynucleotides of the HBV variant with the aid of said probe, as well as kits for detecting HBsAg of the variant or individual epitopes thereof, and antibodies which are specific for the variant or epitopes thereof, such as the methods for detecting polynucleotides, antigen and antibody comprising incubation for forming corresponding complexes and detection of these complexes by suitable methods known to the skilled worker.

Embodiments of these kits and detection methods can be designed for the specific and sole detection of nucleotides and antigen of the HBV variant or antibodies directed against it, or supplementary, i.e. allow detection of the variant analytes of the disclosure in addition to currently known HBV nucleotides, antigens or antibodies.

It is also possible analogously to use an immunogenic mixture of polypeptide sequences of the disclosure in conjunction with known antigens, e.g. for improving the efficacy of a vaccine.

The present disclosure describes a novel variant of the hepatitis B virus (HBV) which has an entirely novel a determinant as a result of amino acid exchanges in the following aa positions of the S-HBsAg sequence. The 1-letter code is used to describe the amino acids.

| aa of HDB 07 | aa Position | aa of ayw2/genotype D |
|---|---|---|
| R | 105 | P |
| L | 110 | I |
| R | 118 | T |
| L | 120 | P |
| K | 122 | R |
| L | 142 | P |
| N | 160 | K |
| P | 173 | L |
| In addition, cysteine (C) is present instead of tyrosine (Y) in position aa 100 of HDB 07: | | |
| C | 100 | Y |

These aa replacements can be attributed to corresponding nucleotide replacements in the corresponding codons.

The present disclosure relates, in some embodiments, to an isolated nucleotide sequence which codes for the a determinant of the virus (FIG. 3 and SEQ ID No: 1).

The disclosure also relates, in some embodiments, nucleotides having at least 65% agreement, preferably at least 75% agreement and particularly preferably having at least 90% agreement with the nucleotide sequence of the present disclosure, or fragments thereof and sequences complementary thereto.

The disclosure also relates, in some embodiments, to polypeptides which are encoded by nucleotide sequences described above, in particular those amino acid sequences which determine the a determinant of HBsAg, and polypeptides which show a similarity of at least 65%, preferably 75% and more preferably 95% to these sequences.

According to some embodiments of the present disclosure, a nucleotide fragment means a consecutive sequence of at least 9, preferably 9-15, particularly preferably 15-21 and in fact very particularly preferably 21-60 nucleotides from the nucleotide sequence of the novel HBV variant, with mixtures of such nucleotide fragments also being obvious.

A polypeptide fragment is understood to be a sequence of at least 3, preferably 3-5, particularly preferably 5-7 and in fact very particularly preferably 7-20 amino acids from the a determinant of the novel HBV variant, this disclosure also encompassing mixtures of such polypeptide fragments according to some embodiments.

The present disclosure also relates, in some embodiments, to an isolated nucleotide sequence which is capable of hybridization and leads to nucleotide sequences which correspond to the nucleotide sequences of the HBsAg of the novel HBV variant or parts of the a determinant of the novel HBV variant, are complementary thereto or are to be ascribed to HDB 07 as subtype or mutation.

The skilled worker is aware that a nucleotide sequence after isolation thereof can be introduced by prior art methods into prokaryotic (e.g. *E. coli*), eukaryotic host cells (e.g. Chinese hamster ovary cell) or yeast (e.g. *S. Cerevisiae*) with the aid of a vector or construct (using methods known to the skilled worker, such as, for example, transfection, transformation or electroporation: Molecular Cloning: A Laboratory Manual, $2^{nd}$ ed., Vol. 1-3, ed Sambrook et al., Cold Spring Harbor Laboratory Press (1989)), it being possible to use transient or permanent cultures.

Accordingly, the present disclosure also relates, in some embodiments, to isolated nucleotide sequences of the a determinant of the novel HBV variant, polypeptides which are encoded by these nucleotides, vectors which comprise nucleotide sequences of the a determinant of the novel HBV variant, as well as the host cell into which a vector is put. Besides the production of polypeptides with the aid of an expression system (recombinantly or by genetic manipulation), the skilled worker is aware that analogous polypeptide structures are also prepared completely synthetically or directly by purification from the virus variant.

It is possible to use the polypeptides or proteins of the novel HBV variant for generating monoclonal and/or polyclonal antibodies which bind immunologically to binding sites (epitopes) of the a determinant of the novel HBV variant. The methods for preparing antibodies are known to the skilled worker (e.g. Koehler et al., Nature 256-494 (1975), Mimms et al., Vi 176: 604-619 (1990)).

It is further possible to use the a determinant of the HDB 07 variant according to some embodiments of the disclosure in the form of the complete polypeptide sequence or parts thereof for determining antibodies directed against the HBV variant (anti-HBsAg antibodies) (see above).

The skilled worker is familiar with a large number of determination methods in which immune complexes are formed, or the formation thereof is inhibited, with polypeptides from the a determinant of the HBV variant and antibodies of animal or human origin.

A specific embodiment is represented by the so-called enzyme immunoassay, of which a possible assay principle is described by way of example below, but without restricting the teaching of the disclosure thereto:

In the very widely used so-called sandwich principle, epitope-carrying polypeptide or protein sequences immobilized on a suitable support (e.g. microparticles or surface of wells of a microtitration plate) are incubated with the investigation sample. Antibodies bound to the epitopes are detected after removal of excess sample, by a further incubation with epitope-carrying polypeptide or protein sequences which are provided with a probe. A probe frequently employed is an enzyme whose catalytic conversion (after removal of the excess reagent) of a suitable substrate leads to a color reaction which is measured by photometry and whose intensity is proportional to the antibody content present in the sample.

Besides this specific embodiment, methods which are homogeneous in nature are also known (i.e. do not require bound/free separation) and make do entirely without a probe (e.g. agglutination methods), can be evaluated with the naked eye (e.g. radial immunodiffusion) or make use of other probes (e.g. radioactive isotopes or chemiluminescence) or a plurality of probes (such as, for example, the biotin/streptavidin system).

Likewise, the polypeptide structures of the HBV variant HDB 07 can be represented by anti-idiotype antibodies or, by choosing a suitable assay principle, variant-specific monoclonal or polyclonal antibodies can also be used to determine anti-HBs antibodies (e.g. in a competitive assay format). It is likewise known that differentiation of the immunoglobulin classes is also possible by choosing the assay principle (e.g. by the "indirect" method with a second class-specific antibody (e.g. IgG or IgM specific) with a probe or with the aid of the so-called anti-μ principle (IgM specific)). It is of course necessary for the methods and materials (including probe and polypeptide sequences) to be adapted to the particular target.

One of ordinary skill in the art who has the benefit of the present disclosure will recognize that "determination of antibodies which are specific for the a determinant of the novel HDB 07 variant" with the present disclosure may include, according to some embodiments, all methods suitable for detecting immunoglobulins and/or immunoglobulin classes directed against the novel HBV variant HDB 07, irrespective of whether the antibody against the novel variant is sought alone or in conjunction with antibodies against known a determinants and/or known mutations in the a region.

Finally, the skilled worker is likewise aware of using monoclonal or polyclonal antibodies or mixtures thereof or fragments of such antibodies or mixtures thereof which react with epitopes of the novel HBV variant HDB 07, to determine the a determinant of the HBV variant according to some embodiments of the disclosure (HBsAg of HDB 07 variant) in the form of the complete polypeptide sequence or parts thereof in investigation samples.

The skilled worker is familiar with a large number of determination methods in which immune complexes are formed, or the formation thereof is inhibited, with one or more monoclonal antibody(s) or polyclonal antibodies (or mixtures thereof or fragments or mixtures of fragments) which are specific for the a determinant of the HBV variant.

A specific embodiment is represented by the so-called enzyme immunoassay, of which a possible assay principle is described by way of example below, but without restricting the concept of the disclosure thereto:

In the very widely used so-called sandwich principle, antibodies or fragments thereof immobilized on a suitable support (e.g. microparticles or surface of wells of a microtitration plate) are incubated with the investigation sample. HBsAg bound to the antibodies is detected after removal of excess sample, by further incubation with anti-HBs antibodies (monoclonal or polyclonal or fragments or mixtures of these fragments) which are provided with a probe. The probe frequently employed is an enzyme whose catalytic conversion (after removal of the excess reagent) of a suitable substrate leads to a color reaction which is measured by photometry and whose intensity is proportional to the antibody content present in the sample.

Besides this specific embodiment, methods which are homogeneous in nature are also known (i.e. do not require bound/free separation) and make do entirely without a probe (e.g. agglutination methods), can be evaluated with the naked eye (e.g. radial immunodiffusion) or make use of other probes (e.g. radioactive isotopes or chemiluminescence) or a plurality of probes (such as, for example, the biotin/streptavidin system).

One of ordinary skill in the art who has the benefit of the present disclosure will recognize that "determination of HBsAg of the novel HBV variant" with the present disclosure may include, according to some embodiments, all methods suitable for detecting polypeptide sequences or antigens of the novel HBV variant, irrespective of whether the HBsAg of the novel variant is determined alone or in conjunction with HBsAg of other determinants and/or known mutations in the a region.

One of ordinary skill in the art having the benefit of the present disclosure will recognize that combining, for economic reasons, an HBsAg determination with a detection method for detecting a further analyte (e.g. HIV antigen or the simultaneous determination of HBV variants HBsAg and specific antibodies directed against it) in one assay mixture (differentiating or non-differentiating).

In relation to nucleic acid assaying (NAA), one of ordinary skill in the art having the benefit of the present disclosure will likewise recognize using nucleotide sequences according to some embodiments of the present disclosure in order to prepare DNA oligomers of 6-8 nucleotides or larger, which are suitable as hybridization probes for detecting the viral genome of the HBV variant described herein in people possibly carrying the virus variant HDB 07, or for example in the blood-donation sector to screen stored blood for the presence of the variant genome either specifically or in combination with detection of nucleotide sequences of known HBV variants and/or HBV mutants. It is likewise possible on the basis of the found nucleotide sequences of the novel HBV variant to develop corresponding primers.

The disclosure further includes a vaccine comprising a polypeptide according to the present disclosure and a conventional adjuvant (e.g. Freund's adjuvant, phosphate-buffered saline or the like). A vaccine of this type can be used to induce the formation of antibodies in mammals, including humans. Similarly, the disclosure includes a particle which comprises a non-variant-specific amino acid sequence which induces a particle formation together with an epitope-containing polypeptide which is specific for the HBV variant HDB 07 of the disclosure.

The present disclosure also relates, in some embodiments, to diagnostic reagents assembled as kits which, based on the methods described above, a detection of HBV variant-specific antigen (HBsAg) or antibodies directed against it (anti-HBs), either as single determinations or combinable with one another or with other known HBV antigens or antibodies specifically reacting therewith, or else with different analytes.

In addition, the present nucleotide sequences can be used to prepare primers and/or gene probes, which is why the disclosure likewise relates, in some embodiments, to kits comprising primers and/or probes for detecting HBV variant-specific nucleic acid either alone or in combination with known HBV nucleotide sequences in investigation samples.

Nucleotide sequences according to the present disclosure can also be used to prepare so-called antisense oligonucleotides (where appropriate for therapeutic purposes).

It is consequently possible to develop on the basis of the present nucleotide sequences primers which are used in the so-called polymerase chain reaction (PCR). PCR is a method for amplifying a desired nucleotide sequence of a nucleic acid or of a nucleic acid mixture. This entails the primers being in each case specifically extended by a polymerase with the desired nucleic acid as reading frame. After dissociation from the original strand, new primers are hybridized and again extended by the polymerase. Repetition of these cycles achieves enrichment of the target sequence molecules sought.

The present disclosure also includes cultures of tissue cells which are infected with a HBV variant according to some embodiments of the disclosure, as well as an isolated HBV variant itself. The disclosure also relates, in some embodiments, to an immunogenic preparation which comprises the attenuated or inactivated HDB 07 variant according to the disclosure of HBV.

The present disclosure is additionally described in the claims.

EXAMPLES

Some specific example embodiments of the disclosure may be illustrated by one or more of the examples provided herein.

Example 1

HBsAg Determination by Enzyme Immunoassay, EIA

The enzyme immunoassay Enzygnost® HBsAg 5.0 from Dade Behring Marburg GmbH, Marburg (Germany), was used to determine the surface antigen (HBsAg) of HBV in the blood of the patient from Berlin.

This is an efficient assay which is approved in Europe and which was carried out in accordance with the statements in the package insert.

The underlying assay principle is a so-called sandwich assay in microtitration plate format:

100 µl of the sample to be investigated are brought into contact in a one-step method with 25 µl of conjugate 1 (murine monoclonal HBsAg-specific antibodies which are covalently labeled with biotin) and immobilized sheep HBsAg-specific polyclonal antibodies. After incubation at 37° C. for 60 minutes and removal of excess components by washing the plate wells 4 times, 100 µl of conjugate 2 which consists of streptavidin to which the probe enzyme peroxidase is covalently bonded are added.

After incubation at 37° C. for 30 minutes and removal of excess components by washing the plate wells 4 times, 75 µl of chromogen buffer/substrate solution are added, followed by incubation at room temperature for 30 minutes. Development of the blue-colored tetramethylbenzidine dye is stopped by adding 75 µl of stop solution (sulfuric acid), and the dye is measured by photometry at 450 nm.

The intensity of the color development, measured by the optical density (O.D.), is directly proportional to the HBsAg content in the investigation sample, and an O.D. value (light absorption value) lower than a limit is assessed as HBsAg-negative. The limit is defined as the average O.D. of the control which is assayed in parallel, negative (present in the assay kit), to which a constant amount of 0.05 O.D. is added.

The limits of detection of the batch used for the investigation (#35214) were ascertained using the internationally accepted standard preparations from the Paul-Ehrlich Institute, Langen, Germany, by graphic interpolation from assays of dilutions of the standard preparations in HBsAg-negative serum as 0.007 ng of ad subtype/ml and 0.005 ng of ay subtype/ml.

Investigation of the sample #126734/305024817, from which the DNA was also isolated, gave results, in 2 independent tests on two different days, between 0.02 and 0.03 O.D., which are to be interpreted according to the criteria of the assay as HBsAg-negative. The included control, positive (present in the assay kit), was positive (validation criteria satisfied).

Example 2

Isolation of HDB 07 DNA from Sample #126734/305024817

A 65 µl aliquot of the Berlin sample was made up to a volume of 200 µl with 135 µl of negative plasma, and the DNA was isolated by using the QIA Amp® Min Elute™ Virus Spin kit from Qiagen, Hilden (Germany). This entailed following all the steps in the method as described in the package insert and carrying out the elution in a volume of 20 µl in each case.

Example 3

Polymerase Chain Reaction, PCR 3.1. HBV Primers

The four following HBV primers were used:

Primer 1 with the 5'>3' sequence:

```
GGGTCACCATATTCTTGGGAAC     (SEQ ID No: 28)
```

Primer 2 with the 5'>3' sequence:

```
TATACCCAAAGACAAAAGAAAATTGG  (SEQ ID No: 29)
```

Primer 3 with the 5'>3' sequence:

```
GACTCGTGGTGGACTTCTCTC      (SEQ ID No: 30)
```

Primer 4 with the 5'>3' sequence:

```
TACAGACTTGGCCCCCAATACC     (SEQ ID No: 31)
```

3.2. PCR Amplification

A so-called nested PCR amplification of the surface antigen was carried out, using the Perkin Elmer Ampli Taq® DNA polymerase kit and the Gene Amp® PCR 9700 thermocycler system from Perkin Elmer Applied Biosystems, USA.

The nucleotides were purchased from Amersham Biosciences, UK.

For the first amplification cycle, 7 µl of the isolated DNA were amplified using primers 1 and 2 mentioned above, and the following conditions:

PCR 1 rxn

| | | |
|---|---|---|
| Primer 1 (10 µM) | 1 µl | |
| Primer 2 (10 µM) | 1 µl | |
| 10× conc. buffer (incl. 15 mM Mg2Cl) | 5 µl | |
| dNTP mix (10 mM) | 1 µl | |
| Dist. water | 34.75 µl | |
| Ampli Taq (5 U/µl) | 0.25 µl | |
| per tube | 43 µl | total volume |
| plus | 7 µl | of isolated DNA |
| | 50 µl | reaction volume |

50 µl reaction mixture was amplified using the described thermocycler under the following conditions:

94° C., 1 min./94° C., 28 sec.—50° C., 28 sec.—72° C., 60 sec. (40 cycles)/72° C., 5 min./8° C. soak.

In the second amplification round, 7 µl of the first PCR product was further amplified using HBV primers 3 and 4 and the following conditions:

PCR 2 rxn

| | | | |
|---|---|---|---|
| Primer 3 (10 µM) | 1 | µl | |
| Primer 4 (10 µM) | 1 | µl | |
| 10× conc. buffer | 5 | µl | |
| dNTP mix (10 mM) | 1 | µl | |
| Dist. water | 34.75 | µl | |
| Ampli Taq (5 U/µl) | 0.25 | µl | |
| per tube | 43 | µl | total volume |
| plus | 7 | µl | PCR product from rxn |
| | 50 | µl | reaction volume |

This PCR 2 mixture was amplified using the thermocycler described above, applying the following conditions:

94° C., 1 min./94° C., 28 sec.—55° C., 28 sec.—72° C., 38 sec. (40 cycles)/72° C., 5 min./8° C. soak.

Finally, the PCR 2 product was fractionated by electrophoresis (1.5% agarose) including suitable molecular weight markers. The PCR product (with about 520 base pairs) was purified using the QIA quick PCR purification kit from Qiagen, Hilden (Germany).

Example 4

Sequencing of HDB 07

The purified PCR product was sequenced by Eurofin Medigenomix GmbH, Martinsried (Germany) using the ABI 3700 capillary system in conjunction with the ABI BigDye Terminator Chemistry Version 3.1. and the ABI Sequencing Analysis Software Version 3.7. and using primers 3 and 4 described in Example 3.

Sequencing Result

It was possible to show that the HBsAg of the analyzed sample shows within the sequenced region the best agreement of the nucleotide and amino acid sequence with genotype D, subtype ayw2. In the region of the a determinant, the analyzed sample from Berlin shows a total of 7 amino acid replacements compared with genotype D, subtype ayw2 (see also FIG. 6):

| | HDB 07: | | D, ayw2: |
|---|---|---|---|
| 1) | Arg (R) | instead of | 105 Pro (P) |
| 2) | Arg (R) | instead of | 118 Thr (T) |
| 3) | Leu (L) | instead of | 120 Pro (P) |
| 4) | Lys (K) | instead of | 122 Arg (R) |
| 5) | Leu (L) | instead of | 142 Pro (P) |
| 6) | Asn (N) | instead of | 160 Lys (K) |
| 7) | Pro (P) | instead of | 173 Leu (L) |
| 8) | Leu (L) | instead of | 110 Ile (I) |
| In addition, there is an amino acid replacement in position # 100: | | | |
| 9) | Tyr (Y) | instead of | 100 Cys (C). |

What is claimed is:

1. An isolated oligo- or polypeptide comprising an amino acid sequence selected from the group consisting of:

an amino acid sequence which has at least 93% identity with SEQ ID No: 5;

an amino acid sequence of SEQ ID No: 5 in which up to five amino acids in

SEQ ID No: 5 are replaced, deleted or inserted; and a fragment of an HBs antigen of a hepatitis B virus comprising an S-HBsAg sequence comprising, at the respective position of the S-HBsAg sequence, arginine at position 105, arginine at position 118, leucine at position 120, leucine at position 142, asparagine at position 160 and proline at position 173.

2. An isolated oligo- or polypeptide comprising:

an S-HBsAg sequence comprising, at the respective position of the S-HBsAg sequence, arginine at position 105, arginine at position 118, leucine at position 120, leucine at position 142, asparagine at position 160 and proline at position 173, wherein the oligo- or polypeptide reacts with sera from individuals infected by the hepatitis B variant HDB 07.

3. The isolated oligo- or polypeptide according to claim 1, wherein the oligo- or polypeptide comprises an amino acid sequence of SEQ ID No: 5.

4. A method for preparing an isolated oligo or polypeptide according to claim 1 comprising culturing a cell under suitable conditions such that the oligo or polypeptide is expressed, wherein the cell comprises a vector or plasmid encoding the oligo- or polypeptide.

5. The method according to claim 4, further comprising obtaining the oligo- or polypeptide from the cell and separating it from other oligo- or polypeptides.

6. An isolated immunogenic peptide or mixture of isolated immunogenic peptides comprising:

one or more isolated oligo- or polypeptides comprising an amino acid sequence selected from the group consisting of:

an amino acid sequence which has at least 93% identity with SEQ ID No: 5;

an amino acid sequence of SEQ ID No: 5 in which up to five amino acids in SEQ ID No: 5 are replaced, deleted or inserted; and a fragment of an HBs antigen of a hepatitis B virus comprising an S-HBsAg sequence comprising, at the respective position of the S-HBsAg sequence, arginine at position 105, arginine at position 118, leucine at position 120, leucine at position 142, asparagine at position 160 and proline at position 173.

7. An isolated oligo- or polypeptide comprising an amino acid sequence selected from the group consisting of:

an amino acid sequence which has at least 97% identity with SEQ ID No: 5; and an amino acid sequence of SEQ ID No: 5 in which up to four amino acids in SEQ ID No: 5 are replaced, deleted or inserted.

* * * * *

SEQUENCE LISTING

```
<160> NUMBER OF SEQ ID NOS: 31

<210> SEQ ID NO 1
<211> LENGTH: 678
<212> TYPE: DNA
<213> ORGANISM: Hepatitis B virus

<400> SEQUENCE: 1

atggagaaca tcacatcagg attcctagga cccctgctcg tgttacaggc ggggtttttc      60

ttgttgacaa gaatcctcac aataccgcag agtctagact cgtggtggac ttctctcaat     120

tttctagggg gaactaccgt gtgtcttggc caaaattcgc agtccccaac ctccaatcac     180

tcaccaacct cctgtcctcc aacttgtcct ggttatcgct ggatgtgtct gcggcgtttt     240

atcatcttcc tcttcatcct gctgctatgc ctcatcttct tgttggttct tctggactgt     300

caaggtatgt tacgcgtttg tcctctactt ccaggatctt caaccaccag caggggacta     360

tgcaaaacct gcacgactcc tgctcaagga acctctatgt atccctcctg ttgctgtacc     420

aaactttcgg acggaaattg cacctgtatt cccatcccat catcctgggc tttcggaaac     480

ttcctatggg agtgggcctc agcccgtttc tcctggccca gtttactagt gccatttgtt     540

cagtggttcg tagggctttc ccccactgtt tggctttcag ttatatggat gatgtggtat     600

tgggggccaa gtctgtacag catcttgagt cccttttac cgctgttacc aattttcttt      660

tgtctttggg tatacatt                                                   678


<210> SEQ ID NO 2
<211> LENGTH: 243
<212> TYPE: DNA
<213> ORGANISM: Hepatitis B virus
```

<400> SEQUENCE: 2

```
tgtcaaggta tgttacgcgt ttgtcctcta cttccaggat cttcaaccac cagcagggga     60

ctatgcaaaa cctgcacgac tcctgctcaa ggaacctcta tgtatccctc ctgttgctgt    120

accaaacttt cggacggaaa ttgcacctgt attcccatcc catcatcctg ggctttcgga    180

aacttcctat gggagtgggc ctcagcccgt ttctcctggc ccagtttact agtgccattt    240

gtt                                                                  243
```

<210> SEQ ID NO 3
<211> LENGTH: 226
<212> TYPE: PRT
<213> ORGANISM: Hepatitis B virus

<400> SEQUENCE: 3

```
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Cys Gln Gly Met Leu Arg Val Cys Pro Leu Leu Pro Gly
            100                 105                 110

Ser Ser Thr Thr Ser Arg Gly Leu Cys Lys Thr Cys Thr Thr Pro Ala
        115                 120                 125

Gln Gly Thr Ser Met Tyr Pro Ser Cys Cys Cys Thr Lys Leu Ser Asp
    130                 135                 140

Gly Asn Cys Thr Cys Ile Pro Ile Pro Ser Ser Trp Ala Phe Gly Asn
145                 150                 155                 160

Phe Leu Trp Glu Trp Ala Ser Ala Arg Phe Ser Trp Pro Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Leu Pro Ile Phe Phe Cys Leu Trp Val
    210                 215                 220

Tyr Ile
225
```

<210> SEQ ID NO 4
<211> LENGTH: 91
<212> TYPE: PRT
<213> ORGANISM: Hepatitis B virus

<400> SEQUENCE: 4

```
Cys Gln Gly Met Leu Arg Val Cys Pro Leu Leu Pro Gly Ser Ser Thr
1               5                   10                  15

Thr Ser Arg Gly Leu Cys Lys Thr Cys Thr Thr Pro Ala Gln Gly Thr
            20                  25                  30
```

-continued

```
Ser Met Tyr Pro Ser Cys Cys Cys Thr Lys Leu Ser Asp Gly Asn Cys
        35                  40                  45

Thr Cys Ile Pro Ile Pro Ser Ser Trp Ala Phe Gly Asn Phe Leu Trp
    50                  55                  60

Glu Trp Ala Ser Ala Arg Phe Ser Trp Pro Ser Leu Leu Val Pro Phe
65                  70                  75                  80

Val Gln Trp Phe Val Gly Leu Ser Pro Thr Val
                85                  90


<210> SEQ ID NO 5
<211> LENGTH: 81
<212> TYPE: PRT
<213> ORGANISM: Hepatitis B virus

<400> SEQUENCE: 5

Cys Gln Gly Met Leu Arg Val Cys Pro Leu Leu Pro Gly Ser Ser Thr
1               5                   10                  15

Thr Ser Arg Gly Leu Cys Lys Thr Cys Thr Thr Pro Ala Gln Gly Thr
            20                  25                  30

Ser Met Tyr Pro Ser Cys Cys Cys Thr Lys Leu Ser Asp Gly Asn Cys
        35                  40                  45

Thr Cys Ile Pro Ile Pro Ser Ser Trp Ala Phe Gly Asn Phe Leu Trp
    50                  55                  60

Glu Trp Ala Ser Ala Arg Phe Ser Trp Pro Ser Leu Leu Val Pro Phe
65                  70                  75                  80

Val


<210> SEQ ID NO 6
<211> LENGTH: 5
<212> TYPE: PRT
<213> ORGANISM: Hepatitis B virus

<400> SEQUENCE: 6

Ser Thr Thr Ser Arg
1               5


<210> SEQ ID NO 7
<211> LENGTH: 5
<212> TYPE: PRT
<213> ORGANISM: Hepatitis B virus

<400> SEQUENCE: 7

Thr Thr Ser Arg Gly
1               5


<210> SEQ ID NO 8
<211> LENGTH: 5
<212> TYPE: PRT
<213> ORGANISM: Hepatitis B virus

<400> SEQUENCE: 8

Thr Ser Arg Gly Leu
1               5


<210> SEQ ID NO 9
<211> LENGTH: 5
<212> TYPE: PRT
<213> ORGANISM: Hepatitis B virus

<400> SEQUENCE: 9

Ser Arg Gly Leu Cys
1               5
```

-continued

<210> SEQ ID NO 10
<211> LENGTH: 5
<212> TYPE: PRT
<213> ORGANISM: Hepatitis B virus

<400> SEQUENCE: 10

Arg Gly Leu Cys Lys
1               5

<210> SEQ ID NO 11
<211> LENGTH: 5
<212> TYPE: PRT
<213> ORGANISM: Hepatitis B virus

<400> SEQUENCE: 11

Gly Leu Cys Lys Thr
1               5

<210> SEQ ID NO 12
<211> LENGTH: 5
<212> TYPE: PRT
<213> ORGANISM: Hepatitis B virus

<400> SEQUENCE: 12

Leu Cys Lys Thr Cys
1               5

<210> SEQ ID NO 13
<211> LENGTH: 5
<212> TYPE: PRT
<213> ORGANISM: Hepatitis B virus

<400> SEQUENCE: 13

Trp Ala Phe Gly Asn
1               5

<210> SEQ ID NO 14
<211> LENGTH: 5
<212> TYPE: PRT
<213> ORGANISM: Hepatitis B virus

<400> SEQUENCE: 14

Ala Phe Gly Asn Phe
1               5

<210> SEQ ID NO 15
<211> LENGTH: 5
<212> TYPE: PRT
<213> ORGANISM: Hepatitis B virus

<400> SEQUENCE: 15

Phe Gly Asn Phe Leu
1               5

<210> SEQ ID NO 16
<211> LENGTH: 5
<212> TYPE: PRT
<213> ORGANISM: Hepatitis B virus

<400> SEQUENCE: 16

Gly Asn Phe Leu Trp
1               5

<210> SEQ ID NO 17
<211> LENGTH: 5
<212> TYPE: PRT
<213> ORGANISM: Hepatitis B virus

<400> SEQUENCE: 17

Asn Phe Leu Trp Glu
1 5

<210> SEQ ID NO 18
<211> LENGTH: 12
<212> TYPE: DNA
<213> ORGANISM: Hepatitis B virus

<400> SEQUENCE: 18
agcaggggac ta 12

<210> SEQ ID NO 19
<211> LENGTH: 18
<212> TYPE: DNA
<213> ORGANISM: Hepatitis B virus

<400> SEQUENCE: 19
agcaggggac tatgcaaa 18

<210> SEQ ID NO 20
<211> LENGTH: 24
<212> TYPE: DNA
<213> ORGANISM: Hepatitis B virus

<400> SEQUENCE: 20
agcaggggac tatgcaaaac ctgc 24

<210> SEQ ID NO 21
<211> LENGTH: 45
<212> TYPE: DNA
<213> ORGANISM: Hepatitis B virus

<400> SEQUENCE: 21
agcaggggac tatgcaaaac ctgcacgact cctgctcaag gaacc 45

<210> SEQ ID NO 22
<211> LENGTH: 81
<212> TYPE: DNA
<213> ORGANISM: Hepatitis B virus

<400> SEQUENCE: 22
agcaggggac tatgcaaaac ctgcacgact cctgctcaag gaacctctat gtatccctcc 60
tgttgctgta ccaaactttc g 81

<210> SEQ ID NO 23
<211> LENGTH: 12
<212> TYPE: DNA
<213> ORGANISM: Hepatitis B virus

<400> SEQUENCE: 23
ttcggaaact tc 12

<210> SEQ ID NO 24
<211> LENGTH: 18
<212> TYPE: DNA
<213> ORGANISM: Hepatitis B virus

<400> SEQUENCE: 24
tgggctttcg gaaacttc 18

<210> SEQ ID NO 25
<211> LENGTH: 27
<212> TYPE: DNA
<213> ORGANISM: Hepatitis B virus

<400> SEQUENCE: 25
ccatcatcct gggctttcgg aaacttc 27

<210> SEQ ID NO 26
<211> LENGTH: 48
<212> TYPE: DNA
<213> ORGANISM: Hepatitis B virus

<400> SEQUENCE: 26
aattgcacct gtattcccat cccatcatcc tgggctttcg gaaacttc 48

<210> SEQ ID NO 27
<211> LENGTH: 81
<212> TYPE: DNA
<213> ORGANISM: Hepatitis B virus

<400> SEQUENCE: 27
ccctcctgtt gctgtaccaa actttcggac ggaaattgca cctgtattcc catcccatca 60
tcctgggctt tcggaaactt c 81

<210> SEQ ID NO 28
<211> LENGTH: 22
<212> TYPE: DNA
<213> ORGANISM: Hepatitis B virus

<400> SEQUENCE: 28
gggtcaccat attcttggga ac 22

<210> SEQ ID NO 29
<211> LENGTH: 26
<212> TYPE: DNA
<213> ORGANISM: Hepatitis B virus

<400> SEQUENCE: 29
tatacccaaa gacaaaagaa aattgg 26

<210> SEQ ID NO 30
<211> LENGTH: 21
<212> TYPE: DNA
<213> ORGANISM: Hepatitis B virus

<400> SEQUENCE: 30
gactcgtggt ggacttctct c 21

<210> SEQ ID NO 31
<211> LENGTH: 22
<212> TYPE: DNA
<213> ORGANISM: Hepatitis B virus

<400> SEQUENCE: 31
tacagacttg gcccccaata cc 22